United States Patent
Cruise et al.

(10) Patent No.: US 11,857,694 B2
(45) Date of Patent: *Jan. 2, 2024

(54) PARTICLES

(71) Applicant: MicroVention, Inc., Aliso Viejo, CA (US)

(72) Inventors: Gregory M. Cruise, Rancho Santa Margarita, CA (US); Steve Plotkin, Aliso Viejo, CA (US); Xinping Wu, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/678,891

(22) Filed: Feb. 23, 2022

(65) Prior Publication Data

US 2022/0176012 A1 Jun. 9, 2022

Related U.S. Application Data

(63) Continuation of application No. 17/010,708, filed on Sep. 2, 2020, now Pat. No. 11,285,240, which is a continuation of application No. 16/717,965, filed on Dec. 17, 2019, now Pat. No. 10,792,390, which is a continuation of application No. 16/505,326, filed on Jul. 8, 2019, now Pat. No. 10,543,295, which is a continuation of application No. 16/184,862, filed on Nov. 8, 2018, now Pat. No. 10,383,973, which is a continuation of application No. 15/878,294, filed on Jan. 23, 2018, now Pat. No. 10,155,064, which is a continuation of application No. 15/081,648, filed on Mar. 25, 2016, now Pat. No. 9,907,880.

(60) Provisional application No. 62/138,859, filed on Mar. 26, 2015.

(51) Int. Cl.
*A61L 24/06* (2006.01)
*A61L 24/00* (2006.01)
*C08F 222/38* (2006.01)

(52) U.S. Cl.
CPC .......... *A61L 24/06* (2013.01); *A61L 24/001* (2013.01); *C08F 222/385* (2013.01); *A61L 2430/36* (2013.01)

(58) Field of Classification Search
CPC .............. C08F 220/38; C08F 220/56; C08F 222/1006; C08F 222/385; C08F 2220/382; C08F 2222/408; A61K 9/0029; A61K 9/1635; A61L 24/001; A61L 31/048; A61L 2430/36
See application file for complete search history.

(56) References Cited

U.S. PATENT DOCUMENTS

| | | |
|---|---|---|
| 4,070,348 A | 1/1978 | Kraemer et al. |
| 4,157,323 A | 6/1979 | Yen et al. |
| 4,925,677 A | 5/1990 | Feijen |
| 5,417,982 A | 5/1995 | Modi |
| 5,545,423 A | 8/1996 | Soon-Shiong et al. |
| 5,635,215 A | 6/1997 | Boschetti et al. |
| 5,648,100 A | 7/1997 | Boschetti et al. |
| 5,662,935 A | 9/1997 | Motta |
| 5,759,578 A | 6/1998 | Soon-Shiong et al. |
| 5,879,709 A | 3/1999 | Soon-Shiong et al. |
| 5,906,997 A | 5/1999 | Schwartz et al. |
| 5,922,357 A | 7/1999 | Coombes et al. |
| 5,958,428 A | 9/1999 | Bhatnagar |
| 6,087,450 A | 7/2000 | Breitbach et al. |
| 6,218,440 B1 | 4/2001 | Kitagawa |
| 6,248,363 B1 | 6/2001 | Yoshikawa et al. |
| 6,306,922 B1 | 10/2001 | Hubbell et al. |
| 6,309,669 B1 | 10/2001 | Setterstrom et al. |
| 6,403,569 B1 | 6/2002 | Achterrath |
| 6,548,081 B2 | 4/2003 | Sadozai et al. |
| 6,555,138 B1 | 4/2003 | Karlsson et al. |
| 6,569,463 B2 | 5/2003 | Patel et al. |
| 6,689,374 B2 | 2/2004 | Chu et al. |
| 6,790,456 B2 | 9/2004 | Vogel et al. |
| 6,794,370 B2 | 9/2004 | Achterrath |
| 6,923,988 B2 | 8/2005 | Patel et al. |
| 6,946,146 B2 | 9/2005 | Muyle |
| 7,070,809 B2 | 7/2006 | Goupil et al. |
| 7,094,369 B2 | 8/2006 | Buiser et al. |
| 7,144,588 B2 | 12/2006 | Oray et al. |
| 7,153,572 B2 | 12/2006 | Cooper et al. |
| 7,442,385 B2 | 10/2008 | Lewis et al. |
| 7,449,236 B2 | 11/2008 | Lanphere et al. |
| 7,462,366 B2 | 12/2008 | Lanphere et al. |
| 7,588,780 B2 | 9/2009 | Buiser et al. |
| 7,591,993 B2 | 9/2009 | Boschetti |

(Continued)

FOREIGN PATENT DOCUMENTS

| | | |
|---|---|---|
| CN | 103709323 A | 4/2014 |
| EP | 0240424 B1 | 5/1991 |

(Continued)

OTHER PUBLICATIONS

European Search Report and Search Opinion dated Jul. 10, 2017 for European Patent Application Serial No. 14859554.9.

International Search Report and Written Opinion dated Dec. 20, 2017 for International Application No. PCT/US2017/054118 filed on Sep. 28, 2017.

International Search Report and Written Opinion dated Feb. 27, 2018 for International Application No. PCT/US2017/054113 filed on Sep. 28, 2017.

(Continued)

*Primary Examiner* — Robert D Harlan
(74) *Attorney, Agent, or Firm* — K&L Gates LLP; Brian J. Novak; Benjamin D. Heuberger

(57) ABSTRACT

Embolic particles are described. The particles are reaction products of a prepolymer solution including at least one polyether macromer and an appropriate monomer.

20 Claims, No Drawings

(56) References Cited

U.S. PATENT DOCUMENTS

| | | |
|---|---|---|
| 7,670,592 B2 | 3/2010 | Boschetti |
| 7,736,671 B2 | 6/2010 | DiCarlo et al. |
| 7,776,240 B2 | 8/2010 | Chu et al. |
| 7,794,755 B2 | 9/2010 | Figuly et al. |
| 7,838,035 B2 | 11/2010 | Figuly |
| 7,838,699 B2 | 11/2010 | Schwarz et al. |
| 7,842,377 B2 | 11/2010 | Lanphere et al. |
| 7,858,119 B1 | 12/2010 | Odidi et al. |
| 7,887,846 B2 | 2/2011 | Figuly |
| 7,897,179 B2 | 3/2011 | Muyle |
| 7,951,402 B2 | 5/2011 | Lanphere et al. |
| 8,062,673 B2 | 11/2011 | Figuly et al. |
| 8,110,226 B2 | 2/2012 | Li |
| 8,143,042 B2 | 3/2012 | Bettinger et al. |
| 8,182,807 B2 | 5/2012 | Labhasetwar et al. |
| 8,201,689 B2 | 6/2012 | Kaern |
| 8,226,926 B2 | 7/2012 | Reb |
| 8,252,302 B2 | 8/2012 | Macdonald |
| 8,323,698 B2 | 12/2012 | Gu et al. |
| 8,323,794 B2 | 12/2012 | Chu et al. |
| 8,329,224 B2 | 12/2012 | Hall et al. |
| 8,367,099 B2 | 2/2013 | Herweck et al. |
| 8,383,758 B2 | 2/2013 | Papisov |
| 8,426,481 B2 | 4/2013 | Hassleholm et al. |
| 8,465,779 B2 | 6/2013 | Cruise et al. |
| 8,470,035 B2 | 6/2013 | Cruise et al. |
| 8,617,132 B2 | 12/2013 | Golzarian et al. |
| 8,673,266 B2 | 3/2014 | Boschetti |
| 8,691,791 B2 | 4/2014 | Lewis et al. |
| 8,697,137 B2 | 4/2014 | Vogel et al. |
| 8,709,384 B2 | 4/2014 | Reb |
| 8,739,978 B2 | 6/2014 | Yoon et al. |
| 8,741,351 B2 | 6/2014 | Vogel et al. |
| 9,408,916 B2 | 8/2016 | Cruise et al. |
| 9,456,823 B2 | 10/2016 | Constant et al. |
| 9,546,236 B2 | 1/2017 | Cruise et al. |
| 9,688,788 B2 | 6/2017 | Plotkin et al. |
| 9,803,043 B2 | 10/2017 | Cruise et al. |
| 9,907,880 B2 | 3/2018 | Cruise et al. |
| 9,938,367 B2 | 4/2018 | Cruise et al. |
| 10,118,980 B1 | 11/2018 | Plotkin et al. |
| 10,144,793 B2 | 12/2018 | Cruise et al. |
| 10,155,064 B2 | 12/2018 | Cruise et al. |
| 10,201,632 B2 | 2/2019 | Hincapie et al. |
| 10,226,533 B2 | 3/2019 | Cruise et al. |
| 10,227,463 B2 | 3/2019 | Cruise et al. |
| 10,328,175 B2 | 6/2019 | Cruise et al. |
| 10,383,973 B2 | 8/2019 | Cruise et al. |
| 10,400,051 B2 | 9/2019 | Cruise et al. |
| 10,519,264 B2 | 12/2019 | Plotkin et al. |
| 10,543,295 B2 | 1/2020 | Cruise et al. |
| 10,632,226 B2 | 4/2020 | Hincapie et al. |
| 10,729,805 B2 | 8/2020 | Cruise et al. |
| 10,792,390 B2 * | 10/2020 | Cruise ................ A61L 24/06 |
| 11,104,772 B2 | 8/2021 | Cruise et al. |
| 11,110,198 B2 | 9/2021 | Hincapie et al. |
| 11,135,167 B2 | 10/2021 | Cruise et al. |
| 11,261,274 B2 | 3/2022 | Plotkin et al. |
| 11,285,240 B2 * | 3/2022 | Cruise ................ A61L 24/001 |
| 2002/0028243 A1 | 3/2002 | Masters |
| 2002/0068089 A1 | 6/2002 | Vogel et al. |
| 2002/0071855 A1 | 6/2002 | Sadozai et al. |
| 2002/0071869 A1 | 6/2002 | Bures et al. |
| 2002/0197326 A1 | 12/2002 | Vogel et al. |
| 2003/0078339 A1 | 4/2003 | Kiser et al. |
| 2003/0183962 A1 | 10/2003 | Buiser et al. |
| 2003/0206864 A1 | 11/2003 | Mangin |
| 2004/0161466 A1 | 8/2004 | Lewis et al. |
| 2005/0196702 A1 | 9/2005 | Bryant et al. |
| 2005/0267556 A1 | 12/2005 | Shuros et al. |
| 2006/0025560 A1 | 2/2006 | Inoue et al. |
| 2006/0052478 A1 | 3/2006 | Madsen et al. |
| 2006/0057098 A1 | 3/2006 | Sato |
| 2006/0069168 A1 | 3/2006 | Tabata et al. |
| 2006/0222596 A1 | 10/2006 | Askari et al. |
| 2006/0240435 A1 | 10/2006 | Minoura et al. |
| 2006/0251582 A1 | 11/2006 | Reb |
| 2007/0035296 A1 | 2/2007 | Potapov et al. |
| 2007/0213683 A1 | 9/2007 | Cassingham et al. |
| 2007/0237741 A1 | 10/2007 | Figuly et al. |
| 2007/0237742 A1 | 10/2007 | Figuly et al. |
| 2007/0237830 A1 | 10/2007 | Figuly |
| 2007/0237956 A1 | 10/2007 | Figuly et al. |
| 2008/0033366 A1 | 2/2008 | Matson et al. |
| 2008/0039890 A1 | 2/2008 | Matson et al. |
| 2008/0102029 A1 | 5/2008 | Fritz et al. |
| 2008/0113029 A1 * | 5/2008 | Fritz ................ A61K 47/32 424/490 |
| 2008/0220077 A1 | 9/2008 | Vogel et al. |
| 2009/0029077 A1 | 1/2009 | Atanasoska et al. |
| 2009/0092677 A1 | 4/2009 | Richard |
| 2009/0117033 A1 | 5/2009 | O'Gara |
| 2009/0246275 A1 | 10/2009 | O'Gara et al. |
| 2009/0253809 A1 | 10/2009 | Gomurashvili et al. |
| 2010/0022419 A1 | 1/2010 | Reed et al. |
| 2010/0028260 A1 | 2/2010 | Fritz et al. |
| 2010/0040688 A1 | 2/2010 | Elbert et al. |
| 2010/0057027 A1 | 3/2010 | Furno et al. |
| 2010/0166876 A1 | 7/2010 | Lewis et al. |
| 2010/0247667 A1 | 9/2010 | Ariga et al. |
| 2010/0261646 A1 | 10/2010 | Lavik et al. |
| 2011/0009327 A1 | 1/2011 | Hill et al. |
| 2011/0009520 A1 | 1/2011 | Figuly et al. |
| 2011/0033548 A1 | 2/2011 | Lai et al. |
| 2011/0033608 A1 | 2/2011 | Figuly et al. |
| 2011/0038936 A1 | 2/2011 | Griswold et al. |
| 2011/0082427 A1 | 4/2011 | Golzarian et al. |
| 2011/0091550 A1 | 4/2011 | Zhang et al. |
| 2011/0152765 A1 | 6/2011 | Weber et al. |
| 2011/0182998 A1 | 7/2011 | Reb et al. |
| 2011/0212179 A1 | 9/2011 | Liu |
| 2012/0129798 A1 | 5/2012 | Akala et al. |
| 2012/0135170 A1 | 5/2012 | Meldal et al. |
| 2012/0213831 A1 | 8/2012 | Vogel et al. |
| 2012/0276151 A1 | 11/2012 | Lewis et al. |
| 2012/0302654 A1 * | 11/2012 | Cruise ................ A61K 9/0024 523/105 |
| 2013/0052142 A1 | 2/2013 | Harder et al. |
| 2013/0190795 A1 | 7/2013 | Matson et al. |
| 2013/0315838 A1 | 11/2013 | Reb et al. |
| 2013/0323306 A1 | 12/2013 | Weber |
| 2014/0030350 A1 | 1/2014 | Ashrafi et al. |
| 2014/0162969 A1 | 6/2014 | Lewis et al. |
| 2014/0186601 A1 | 7/2014 | Chang et al. |
| 2014/0287043 A1 | 9/2014 | Kaplan et al. |
| 2020/0324016 A1 | 10/2020 | Cruise et al. |
| 2021/0361823 A1 | 11/2021 | Hincapie et al. |
| 2021/0401749 A1 | 12/2021 | Cruise et al. |
| 2022/0144990 A1 | 5/2022 | Plotkin et al. |

FOREIGN PATENT DOCUMENTS

| | | |
|---|---|---|
| EP | 1534351 B1 | 10/2006 |
| EP | 1820495 A2 | 8/2007 |
| EP | 1267839 B1 | 10/2007 |
| EP | 2269580 A2 | 1/2011 |
| EP | 2295480 A1 | 3/2011 |
| EP | 1796644 B1 | 4/2011 |
| EP | 1986706 B1 | 8/2011 |
| EP | 2368581 A2 | 9/2011 |
| EP | 2475695 B1 | 4/2014 |
| EP | 2286799 B1 | 7/2015 |
| JP | H05-279416 A | 10/1993 |
| JP | 2003-245544 A | 9/2003 |
| JP | 2006104140 A | 4/2006 |
| JP | 2011-201031 A | 10/2011 |
| JP | 2011-245267 A | 12/2011 |
| JP | 2012-100680 A | 5/2012 |
| JP | 2012-170773 A | 9/2012 |
| JP | 2012-187308 A | 10/2012 |
| JP | 2014-218439 A | 11/2014 |
| WO | 1995/019186 A2 | 7/1995 |
| WO | 2000/078846 A1 | 12/2000 |
| WO | 2001/072281 A2 | 10/2001 |

(56) References Cited

FOREIGN PATENT DOCUMENTS

| WO | 2002/015913 A1 | 2/2002 |
| WO | 2002/071994 A1 | 9/2002 |
| WO | 2003/094930 A1 | 11/2003 |
| WO | 2003/097116 A1 | 11/2003 |
| WO | 2004/081059 A1 | 9/2004 |
| WO | 2006/081517 A2 | 8/2006 |
| WO | 2006/119968 A2 | 11/2006 |
| WO | 2007/035296 A2 | 3/2007 |
| WO | 2007/133020 A1 | 11/2007 |
| WO | 2008/034911 A1 | 3/2008 |
| WO | 2008/047095 A1 | 4/2008 |
| WO | 2008/057163 A2 | 5/2008 |
| WO | 2008/128580 A1 | 10/2008 |
| WO | 2008/136536 A1 | 11/2008 |
| WO | 2009/015281 A2 | 1/2009 |
| WO | 2009/040434 A1 | 4/2009 |
| WO | 2009/073193 A2 | 6/2009 |
| WO | 2009/130332 A1 | 10/2009 |
| WO | 2009/131982 A1 | 10/2009 |
| WO | 2010/063630 A2 | 6/2010 |
| WO | 2011/014722 A2 | 2/2011 |
| WO | 2011/029867 A1 | 3/2011 |
| WO | 2011/068455 A1 | 6/2011 |
| WO | 2012/073188 A1 | 6/2012 |
| WO | 2012/120138 A1 | 9/2012 |
| WO | 2012/121073 A1 | 9/2012 |
| WO | 2012/133737 A1 | 10/2012 |
| WO | 2012/145431 A2 | 10/2012 |
| WO | 2012/145739 A1 | 10/2012 |
| WO | 2012/166594 A1 | 12/2012 |
| WO | 2013/130143 A2 | 9/2013 |
| WO | 2013/177364 A1 | 11/2013 |
| WO | 2014/034787 A1 | 3/2014 |
| WO | 2015/042461 A1 | 3/2015 |
| WO | 2015/042462 A1 | 3/2015 |
| WO | 2015/070094 A1 | 5/2015 |
| WO | 2015/167752 A1 | 11/2015 |
| WO | 2016/154592 A1 | 9/2016 |
| WO | 2018/064389 A1 | 4/2018 |
| WO | 2018/064390 A1 | 4/2018 |

OTHER PUBLICATIONS

U.S. Appl. No. 17/390,680, filed Jul. 30, 2021, now abandoned.
Blinova et al., Poly(ethylene glycol) containing functionalized polymer membranes for carbon dioxide separation. Preprints—American Chemical Society, Division of Energy & Fuels, 59(1):433-434 (2014).
International Search Report and Written Opinion dated Dec. 24, 2014 for International Application No. PCT/US2014/056647 filed on Sep. 19, 2014.
International Search Report and Written Opinion dated Feb. 27, 2015 for International Application No. PCT/US2014/064680 filed on Nov. 7, 2014.
International Search Report and Written Opinion dated Dec. 24, 2014 for International Application No. PCT/US2014/056644 filed on Sep. 19, 2014.
Kamitani et al., Design of cell-surface-retained polymers for artificial ligand display. ChemBioChem, 10(2):230-233 (2009).
Supplementary European Search Report dated Apr. 19, 2017 for European Application No. 14845609.
Supplementary European Search Report dated Apr. 6, 2017 for European Application No. 14845676.7.
International Search Report and Written Opinion dated Jun. 2, 2016 for International Application No. PCT/US2016/024340 filed on Mar. 25, 2016.
Tarasyuk et al., Investigation into the influence of organic modifiers and ultradispersed hybrid fillers on the structure and properties of glass-ceramic coatings prepared by the sol-gel method. Glass Physics and Chemistry, vol. 32, No. 4, pp. 439-447 (2006).

* cited by examiner

PARTICLES

CROSS REFERENCE TO RELATED APPLICATIONS

This application is a continuation of U.S. patent application Ser. No. 17/010,708, filed Sep. 2, 2020, which is a continuation of U.S. patent application Ser. No. 16/717,965, filed Dec. 17, 2019, which is a continuation of U.S. patent application Ser. No. 16/505,326, filed Jul. 8, 2019, now U.S. Pat. No. 10,543,295, which is a continuation of U.S. patent application Ser. No. 16/184,862, filed Nov. 8, 2018, now U.S. Pat. No. 10,383,973, which is a continuation of U.S. patent application Ser. No. 15/878,294, filed Jan. 23, 2018, now U.S. Pat. No. 10,155,064, which is a continuation of U.S. patent application Ser. No. 15/081,648, filed Mar. 25, 2016, now U.S. Pat. No. 9,907,880, which claims the benefit of U.S. provisional patent application No. 62/138,859, filed Mar. 26, 2015, the entire disclosures each of which are incorporated herein by reference.

FIELD

The present invention relates to embolic particles that have a first diameter that can fit through a microcatheter or other delivery device and a second expanded diameter once implanted.

SUMMARY

Described herein generally are embolic particles. These embolic particles can be used for medical purposes such as occluding vascular defects. In some embodiments, the embolic particles described herein can be used to occlude other luminal defects such as those in the bile ducts, urethra, vagina, fallopian tubes, and the like. Embolic particles can include a treated polymer particle containing ionic groups.

The treated polymer particles can have a smaller first diameter when delivered and then swell or otherwise enlarge to a larger second diameter once a certain condition has been met. The condition can be subjecting the treated embolic particles to a physiological condition.

The embolic particles can have a first diameter of between about 40 µm and about 1,200 µm and can enlarge to the second diameter of about 80 µm and about 3,600 µm.

In order to allow the embolic particles to occlude vascular defects, larger particles are desired. However, smaller particles allow delivery through smaller microcatheters. A smaller microcatheter is particularly advantageous in tortuous and/or distal anatomy. Thus, the first diameter described can be smaller than the inner diameter of a microcatheter and the second diameter can be larger than the inner diameter of the microcatheter.

Methods of making and using the polymer particles are also described. In one embodiment, methods of making polymer particles comprise treating polymer particles to render them expandable at a certain condition(s). The polymer particles can be formed by reacting a monomer solution including at least one monomer or macromer, an monomer including ionic groups, optionally a crosslinker, and initiator(s) in a non-solvent to form polymer particles which can be subsequently treated. In some embodiments, the treated polymer particle has a first diameter and a second diameter wherein the second diameter is larger than the first diameter when the treated polymer particle is subjected to a physiological condition.

In one embodiment, the non-solvent is a mineral oil. In another embodiment, the non-solvent is hexane. In another embodiment the non-solvent is water.

In another embodiment, the at least one monomer is any molecule containing a single ethylenic unsaturation. In some embodiments, the monomer is acrylamide. In some embodiments, the monomer is methacrylamide. In some embodiments, the monomer is hydroxyethyl methacrylate.

In another embodiment, the at least one macromer is a polyether such as a derivatized polyether. In some embodiments the polyether macromer is a poly(ethylene glycol) macromer. The derivatized poly(ethylene glycol) macromer can be poly(ethylene glycol) diacrylamide, poly(ethylene glycol) diacrylate, poly(ethylene glycol) dimethacrylate, poly(ethylene glycol) dimethacrylamide, or a combination thereof. In some embodiments, the at least one derivatized poly(ethylene glycol) macromer is poly(ethylene glycol) diacrylamide 10,000.

In another embodiment, the optional crosslinker is any molecule containing a multiplicity of ethylenic unsaturations. In some embodiments, the at least one macromer can function as the crosslinker. In some embodiments, the crosslinker is N,N-methylene bisacrylamide. In other embodiments, the crosslinker is ethylene glycol dimethacrylate. In other embodiments, the crosslinker is glyercerol dimethacrylate.

In some embodiments, the physiological condition can be a condition found in the blood or other bodily fluid such as urine, bile, saliva, vaginal fluids, and the like. In one embodiment, the physiological pH of the blood or other bodily fluid is the condition.

In some embodiments, the treated polymer particle is an acid treated polymer particle. When the treated polymer particle is an acid treated polymer particle, the particle contains carboxylic acid groups. Likewise, in other embodiments, the treated polymer particle is a base treated polymer particle. When the treated polymer particle is a base treated polymer particle, the particle contains amino groups.

If an initiator is utilized, the initiator can be ammonium persulfate, tetramethylethylene diamine, or a combination thereof. In other embodiments, heat sensitive initiators such as azobisisobutyronitrile (AIBN) or a water soluble AIBN derivative is utilized.

DETAILED DESCRIPTION

Described herein generally are devices and methods for occluding vascular or other luminal defects. Devices as used herein can describe embolics and embolic devices generally. In one embodiment, an embolic device can be embolic particles.

Embolic particles can be generally sphere-shaped or a particle-shaped "bead" or "microsphere" made of a biocompatible substance. The embolic particles can be injected through a microcatheter.

Embolic particles as described herein can be delivered to a vascular defect or other lumen by various delivery methods. In one embodiment, a method can start by accessing the aneurysm with a catheter or microcatheter. A flow diverting stent (FDS) is then deployed across the neck of the aneurysm. The flow diverting stent allows the microcatheter to be "jailed" in place. After the microcatheter has been jailed, one or more embolic devices such as, but not limited to beads, foams, particles, or other agents can be delivered through the microcatheter. These embolic devices are physically larger than the maximum pore size of the flow diverting stent. The microcatheter is then removed thereby trapping the embolics within the aneurysm behind the flow diverting stent.

In one embodiment, the embolic particles can be sized to be small enough to travel through a microcatheter without clogging or occluding the mircocatheter, yet large enough so that the particles do not migrate through the flow diverting stent's mesh structure.

In one embodiment, the embolic particles can be small enough to fit through a microcatheter. The microcatheter can have a size of at most about 0.0155", at most about 0.0160", at most about 0.0165", at most about 0.0170", at most about 0.0175", at most about 0.018", at most about 0.019", or at most about 0.02". In one embodiment, the microcatheter can be a 0.0165" (about 420 microns) microcatheter. In another embodiment, a microcatheter can be a Headway Duo.

Also, in one embodiment, the embolic particles can be large enough, or have a large enough average diameter, that they do not migrate through a particular sized mesh. In some embodiments, the mesh can be a mesh opening of a flow diverting stent. The embolic particles described herein, unlike conventional particles can have diameters large enough to be delivered using such a mesh.

In some embodiments, the mesh of a flow diverting stent can include a mesh opening of about 0.006" (about 150 microns). In other embodiments, the mesh size can be at most about 0.04", at most about 0.05", at most about 0.06", at most about 0.07", at most about 0.08", or at most about 0.09". In some embodiments, the flow diverting stent can be a flow re-direction endoluminal device, referred to by the tradename FRED® (MicroVention, Inc. Tustin, CA).

In one embodiment, the size range for the embolic is about 200 microns to about 500 microns.

In other embodiments, in order maximize the size of the embolic particles, the embolic particles can be expansible. In such embodiments, the embolic particles can start at a smaller diameter so that they can be delivered through a smaller microcatheter and then expand at the physiological site to provide maximum volumetric filling.

In one embodiment, for example, the embolic particles can have an initial diameter of about 200 microns to about 500 microns and, after deployment, can expand to about 400 microns to about 1500 microns.

Expansible embolic particles deliverable through a smaller microcatheter can have a number of advantages. First, a smaller microcatheter is easier to navigate through tortuous anatomy, particularly to distal locations. Second, a smaller microcatheter can be used in conjunction with standard flow diverting stent delivery systems (for example, the Headway 27 or Headway 21) in a standard 6F guide catheter, thus avoiding the need to increase the guide catheter size or making a second puncture on the contralateral side, saving the patient from additional injury or potential access site complications. Third, a smaller microcatheter may ensure a tighter seal and smaller opening where the microcatheter is jailed by the flow diverting stent thus reducing the possibility of migration of the embolic during delivery.

The embolic particles described herein may be formed of any material that can expand once delivered to an occlusion site such as a vascular defect. The expansile embolic particles can be any particle containing ionic groups that are pretreated with the appropriate low or high pH solutions to shrink the diameter of the particle.

The embolic particles can be formed by reacting a monomer or prepolymer solution including (i) at least one monomer or macromer, (ii) an monomer including ionic groups, (iii) optionally a crosslinker, and (iv) initiator(s) in a nonsolvent to form polymer particles which can be subsequently treated. The embolic particles can also be formed from a monomer or prepolymer solution or mixture comprising: (i) one or more macromer(s), for example, a macromer that contains at least two functional groups amenable to polymerization, (ii) one or more ionic monomers, and (iii) optionally one or more multifunctional crosslinkers. In some embodiments, a polymerization initiator may be utilized.

In one embodiment, the particle embolics can comprise (i) one or more monomers that contain both a singular functional group amenable to polymerization and ionizable groups and (ii) one or more monomeric or macromeric crosslinkers.

In one embodiment, expansile embolic particles can include various combinations of macromers and optionally monomers. For example, one, two, three or more macromers can be included in the embolic particles. Further, one, two, three or more monomers can be included in the embolic particles.

In one embodiment, the macromer can include a plurality of functional groups suitable or amenable to polymerization. In some embodiments, the macromer can be linear. In other embodiments, the macromer can have one or more branches. In still other embodiments, the macromer can be an ethylenically unsaturated macromer. Macromers can include polyethers. Polyether macromers can include linear or branched poly(ethylene glycol), poly(propylene glycol), poly(tetramethylene oxide), derivatives thereof, or combinations thereof. Macromers can also include linear or branched poly(vinyl alcohol).

Macromers described herein can have molecular weights of about 200 grams/mole, 400 grams/mole, 600 grams/mole, 800 grams/mole, 1,000 grams/mole, 2,000 grams/mole, 3,000 grams/mole, 4,000 grams/mole, 5,000 grams/mole, 10,000 grams/mole, 15,000 grams/mole, 20,000 grams/mole, 25,000 grams/mole, 30,000 grams/mole, 35,000 grams/mole, between about 200 grams/mole and about 35,000 grams/mole, between about 200 grams/mole and about 30,000 grams/mole, between about 200 grams/mole and about 1,000 grams/mole, between about 1,000 grams/mole and about 15,000 grams/mole, at least about 200 grams/mole, at most about 30,000 g/mole, or at most about 35,000 grams/mole. In one embodiment, macromers can have a molecular weight of about 10,000 g/mole.

When used as a crosslinker, a macromer can have a low molecular weight of about 200 grams/mole, 400 grams/mole, 600 grams/mole, 800 grams/mole, 1,000 grams/mole, or between about 200 grams/mole and about 1,000 grams/mole.

Derivatives of these polyethers can be prepared to render them amenable to polymerization. While any type of chemistry can be utilized, for example nucleophile/N-hydroxysuccinimde esters, nucleophile/halide, vinyl sulfone/acrylate or maleimide/acrylate; another type of chemistry can be free radical polymerization. As such, polyethers with a plurality of ethylenically unsaturated groups, such as acrylate, acrylamide, methacrylate, methacrylamide, and vinyl, can be used. In one embodiment, a polyether macromer can be poly(ethylene glycol) diacrylamide with a molecular weight of about 10,000 g/mole.

In another embodiment the macromer is poly(ethylene glycol) diacrylamide, poly(ethylene glycol) diacrylate, poly (ethylene glycol) dimethacrylate, poly(ethylene glycol) dimethacrylamide, derivatives thereof, or combinations thereof.

Macromers can be included at a concentration in the solvent of about 0% w/w, about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 25% w/w, about 30% w/w, about 35% w/w, about 40% w/w, about 45% w/w, about 50% w/w, about 60% w/w, about 70% w/w, between about 5% w/w and about 10% w/w, between about 5% w/w and about 20% w/w, between about 5% w/w and about 25% w/w, between about 5% w/w and about 15% w/w, between about 6% w/w and about 8% w/w, or between about 14% w/w and about 16% w/w. In some embodiments, a macromer need not be used.

In one embodiment, the macromer can be included at a concentration of about 7% w/w in the solvent.

In one embodiment, the macromer can be included at a concentration of about 15% w/w in the solvent.

In one embodiment, the macromer can be included at a concentration of about 16.5% w/w in the solvent.

In one embodiment, the macromer can be included at a concentration of about 17% w/w in the solvent.

In some embodiments, if one of the monomer(s) and/or macromers(s) is a solid, a solvent can be utilized in the preparation of the particles for use as embolics. If liquid monomers and macromers are utilized, a solvent may not be required. In some embodiments, even when using liquid monomers and/or macromers, a solvent may still be used. Solvents may include any liquid that can dissolve or substantially dissolve a macromer, monomers, multifunctional crosslinkers, and/or initiators. Any aqueous or organic solvent may be used that dissolves the desired monomer(s), macromer(s), multifunctional crosslinker(s) and/or polymerization initiators. In one embodiment, the solvent can be water. In another embodiment, the solvent can be dimethyl formamide. Additionally, solutes, e.g. sodium chloride, may be added to the solvent to increase the rate of polymerization. Solvent concentration can be varied to alter the swelling properties of the particles.

Solvent concentrations can be about 25% w/w, about 35% w/w, about 45% w/w, about 55% w/w, about 65% w/w, about 75% w/w, about 85% w/w, about 95% w/w, between about 40% w/w and about 80% w/w, between about 30% w/w and about 90% w/w, or between about 50% w/w and about 70% w/w of the solution. In one embodiment, the solvent concentration can be about 50% w/w, about 51% w/w, about 52% w/w, about 53% w/w, about 54% w/w, about 55% w/w, about 56% w/w, about 57% w/w, about 58% w/w, about 59% w/w, or about 60% w/w. In another embodiment, the solvent concentration can be about 65% w/w, about 66% w/w, about 67% w/w, about 68% w/w, about 69% w/w, about 70% w/w, about 71% w/w, about 72% w/w, about 73% w/w, about 74% w/w, or about 75% w/w. In some embodiments, the concentration of the solvent ranges from about 20% w/w to about 80% w/w or about 50% w/w to about 60% w/w.

In one embodiment, the solvent concentration can be about 57% w/w.

In one embodiment, the solvent concentration can be about 70% w/w.

In one embodiment, the solvent concentration can be about 71.6% w/w.

In one embodiment, the solvent concentration can be about 72% w/w.

In general, monomers can contain moieties such as acrylate, acrylamide, methacrylate, methacrylamide or other moieties amenable to polymerization. In one embodiment, the polymer particles are comprised of one or more macromers combined with one or more monomers.

Optionally, one or more monomers can be added to the macromer to impart desired chemical and/or mechanical properties to the polymer particle.

To reduce the diameter and to allow control of the rate of expansion of the embolic particles, monomers with ionic moieties, e.g. carboxylic acids and amines, can be polymerized into the particle embolic. In some embodiments, monomer(s) can be acidic and ethylenically unsaturated. Such monomers can include acrylic acid, methacrylic acid, 3-sulfopropyl acrylate, 3-sulfopropyl methacrylate, derivatives thereof, combinations thereof, and salts thereof. Preferred basic, ionizable, ethylenically unsaturated monomers include aminoethyl methacrylate, aminopropyl methacrylate, derivatives thereof, combinations thereof, and salts thereof.

Monomers including positive or negative moieties can be present in solution at concentrations of about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 40% w/w, about 50% w/w, about 55% w/w, about 60% w/w, about 65% w/w, about 70% w/w, about 80% w/w, between about 1% w/w and about 15% w/w, between about 1% w/w and about 5% w/w, between about 15% w/w and about 35% w/w, or between about 20% w/w and about 30% w/w. In other embodiments, monomers can be present in the solvent at a range of between about 40% w/w and about 60% w/w.

In one embodiment, sodium acrylate can be included at a concentration of about 12% w/w in the solvent.

In one embodiment, N-(2-aminoethyl)-methacrylate can be included at a concentration of about 3% w/w in the solvent.

In one embodiment, N-(3-aminopropyl) methacrylamide can be included at a concentration of about 24% w/w in the solvent.

In one embodiment, the monomer is not n-isopropyl acrylamide. In other embodiments, the polymer particles described herein do not include n-isopropyl acrylamide.

If desired, uncharged, reactive moieties can be introduced into the particles. For example, hydroxyl groups can be introduced into the particles with the addition of 2-hydroxyethyl acrylate, 2-hydroxyethyl methacrylate, glycerol monomethacrylate, glycerol monoacrylate, sorbitol monomethacrylate, sorbitol monoacrylate, a carbohydrate similar to sorbitol and amenable to polymerization, derivatives thereof, or combinations thereof. Alternatively, uncharged, relatively un-reactive moieties can be introduced into the particles. For example, acrylamide, methacrylamide, methyl methacrylate, derivatives thereof, or combinations thereof can be added to the polyether macromer. In some embodiments, the monomer(s) can be selected to vary the number of hydroxyl groups in the polymeric particles to enable the particles to remain suspended in radiopaque contrast solution used in the preparation of the particle for clinical use.

Further, in other embodiments, monomers may be selected to impart visualization using medically relevant imaging techniques. Visualization of the embolic particles under fluoroscopy can be imparted by the incorporation of solid particles of radiopaque materials such as barium, bismuth, tantalum, platinum, gold, and other dense metals into the hydrogel or by the incorporation of iodine-containing molecules polymerized into the embolic structure. In one embodiment, visualization agents for fluoroscopy are barium sulfate and iodine-containing molecules. Visualization of the embolic particles under computed tomography imaging can be imparted by incorporation of solid particles of barium or bismuth or by the incorporation of iodine-containing molecules polymerized into the embolic structure. Metals visible under fluoroscopy generally result in beam hardening artifacts that preclude the usefulness of computed tomography imaging for medical purposes. In some embodiments, visualization agents for fluoroscopy are barium sulfate or iodine-containing molecules. Concentrations of barium sulfate to render the embolic particles visible using fluoroscopic and computed tomography imaging can range from about 30% to about 60% w/w in the solvent of the prepolymer solution. Concentrations of iodine to render the embolic particles visible using fluoroscopic and computed tomography imaging can range from about 80 to about 300 mg 1/g of particles in the solvent of the prepolymer solution.

Visualization of the embolic particles under magnetic resonance imaging can be imparted by the incorporation of solid particles of superparamagnetic iron oxide or gadolinium molecules polymerized into the embolic structure. In one embodiment, a visualization agent for magnetic resonance can be superparamagnetic iron oxide with a particle size of 10 microns. Concentrations of superparamagnetic iron oxide particles to render the embolic particles visible using magnetic resonance imaging range from 0.1% to 1% w/w in the solvent of the prepolymer solution.

In some embodiments, a visualization agent can be a monomer and incorporated into the polymeric structure.

Monomers incorporating visualization characteristics can include one or more halogen atoms. For example, monomers can include 1, 2, 3, 4, 5, 6, 7 or more halogen atoms. In some embodiments, the halogen atoms can be Br or I. In one embodiment, the halogen atoms are I.

In one embodiment, a monomer including a visualization agent or the characteristics of a visualization agent can have a structure:

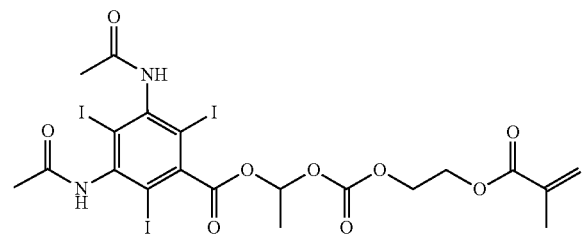 [SMILES: C=C(C)C(=O)OCCOC(=O)OC(C)OC(=O)c1c(I)c(NC(C)=O)c(I)c(NC(C)=O)c1I]

In the above structure, one or more iodine atoms can be replaced by bromine.

In another embodiment, a monomer including a visualization agent or the characteristics of a visualization agent can have a structure:

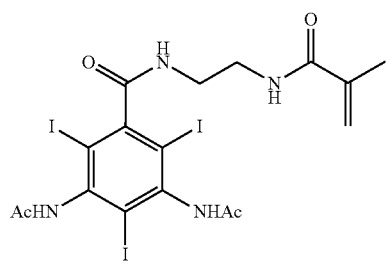 [SMILES: C=C(C)C(=O)NCCNC(=O)c1c(I)c(NC(C)=O)c(I)c(NC(C)=O)c1I]

Again, in the above structure, one or more iodine atoms can be replaced by bromine.

In another embodiment, a monomer including a visualization agent or the characteristics of a visualization agent can have a structure:

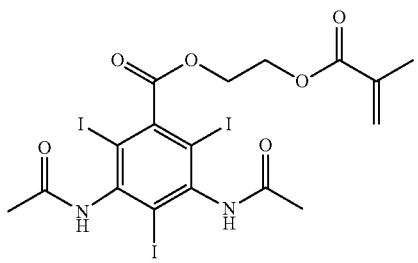 [SMILES: C=C(C)C(=O)OCCOC(=O)c1c(I)c(NC(C)=O)c(I)c(NC(C)=O)c1I]

Again, in the above structure, one or more iodine atoms can be replaced by bromine.

Such uncharged moieties if included can be present in the final particle (not including solvents, initiators, and salts) at about 0% w/w, about 10% w/w, about 20% w/w, about 30% w/w, about 40% w/w, about 50% w/w, about 60% w/w, about 61% w/w, about 62% w/w, about 63% w/w, about 64% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 80% w/w, about 90% w/w, between about 50% w/w and about 90% w/w, between about 60% w/w and about 70% w/w, between about 65% w/w and about 70% w/w, or between about 67% w/w and about 69% w/w.

In one embodiment, an uncharged moiety can be present at about 68% w/w of the final particle.

In one embodiment, multifunctional crosslinkers may be incorporated that contain at least two functional groups suitable to polymerization and at least one linkage susceptible to breakage under physiological conditions to impart biodegradation to the polymer particle. Linkages susceptible to breakage in a physiological environment include those susceptible to hydrolysis, including esters, thioesters, carbamates, oxalates, and carbonates, and those susceptible to enzymatic action, including peptides that are cleaved by matrix metalloproteinases, collagenases, elastases, and cathepsins. Multiple crosslinkers could be utilized to control the rate of degradation in a manner that is not possible with only one.

Crosslinkers described herein include a plurality of polymerizable groups and can join monomers and macromers together thereby permitting the formation of solid embolic particles. Biodegradation can be imparted to the embolic particles by utilizing a crosslinker with linkages susceptible to degradation in a physiological environment. Over time, in vivo the linkages can break thereby unbinding the polymer chains. The judicious selection of monomers permits the formation of water-soluble degradation products that diffuse away and are cleared by the host. Linkages susceptible to hydrolysis, such as esters, thioesters, carbamates, oxalates, and carbonates, or peptides degraded by enzymes are preferred methods of imparting biodegradation to the embolic particles.

Adding multifunctional crosslinkers containing more than one moiety amenable to polymerization can create a more cohesive hydrogel polymer by adding crosslinking to the molecular structure. In some embodiments the polymer particles are comprised of a macromer combined with one or more multifunctional crosslinkers such as, but not limited to, glycerol dimethacrylate, glycerol diacrylate, sorbitol dimethacrylate, sorbitol acrylate, a derivatized carbohydrate similar to sorbitol, derivatives thereof, or combinations thereof. In a preferred embodiment the multifunctional crosslinker is N,N'-methylenebisacrylamide.

In one embodiment, a biodegradable crosslinker can have a structure:

In another embodiment, a biodegradable crosslinker can have a structure:

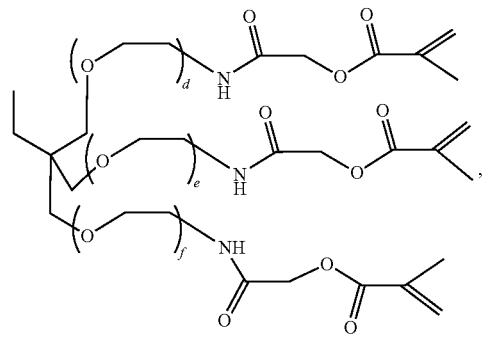

wherein d, e, f, and g are each independently 1-20.

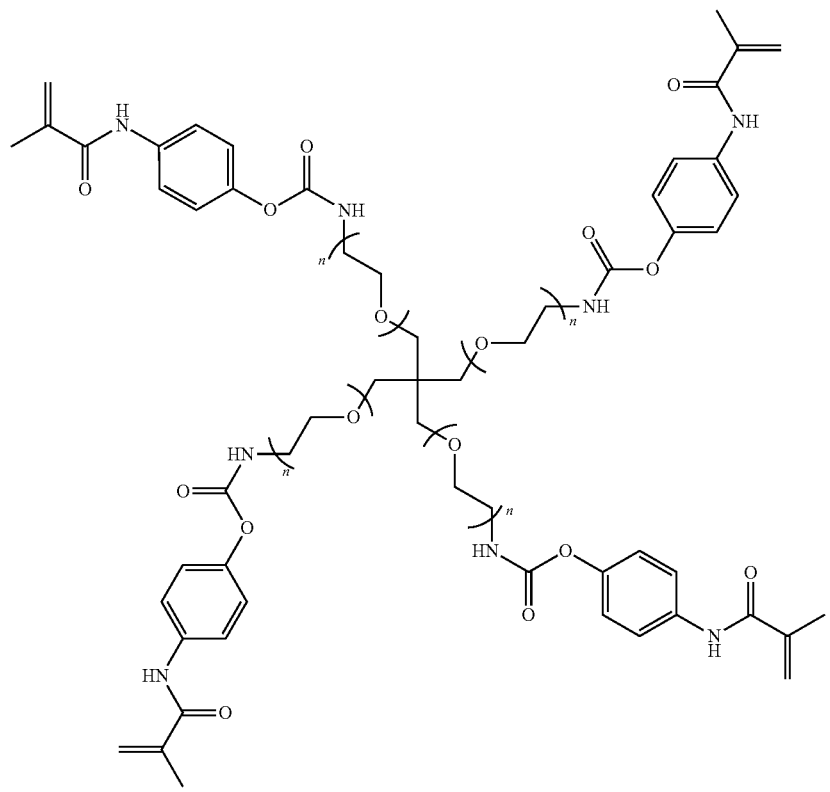

wherein each n is independently 1-20.

In one embodiment, a biodegradable crosslinker can have a structure:

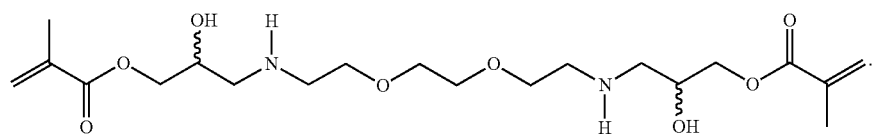 [SMILES: C=C(C)C(=O)OCC(O)CNCCOCCOCCNCC(O)COC(=O)C(=C)C]

In another embodiment, a biodegradable crosslinker can have a structure:

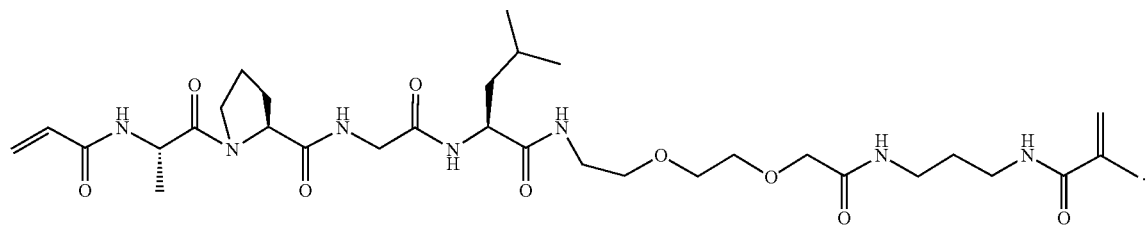 [SMILES: C=CC(=O)N[C@@H](C)C(=O)N1CCC[C@H]1C(=O)NCC(=O)N[C@@H](CC(C)C)C(=O)NCCOCCOCC(=O)NCCCNC(=O)C(=C)C]

If used, a crosslinker can be present in amount of about 0.1% w/w, about 0.25% w/w, about 0.5% w/w, about 0.75% w/w, about 1.0% w/w, about 1.25% w/w, about 1.5% w/w, about 1.75% w/w, about 2% w/w, about 3% w/w, about 4% w/w, about 5% w/w, about 6% w/w, about 7% w/w, about 10% w/w, about 20% w/w, about 25% w/w, about 30% w/w, between about 0% w/w and about 10% w/w, between about 0% w/w and about 2% w/w, between about 0.5% w/w and about 1.5% w/w, between about 0.25% w/w and about 1.75% w/w, or between about 0.1% w/w and about 2% w/w.

In one embodiment, a crosslinker is not used.

In one embodiment, a crosslinker can be present at about 1% w/w.

In one embodiment, the crosslinker can be N,N'-methylenebisacrylamide.

Any amounts of macromer(s), monomer(s), and multifunctional crosslinker(s) can be used that allows for a desired particle. Total concentration of reactive compounds or solids in the solvent can be about 5% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 30% w/w, about 31% w/w, about 32% w/w, about 33% w/w, about 34% w/w, about 35% w/w, about 36% w/w, about 37% w/w, about 38% w/w, about 39% w/w, 40% w/w, about 50% w/w, about 60% w/w, about 70% w/w, between about 10% and 60%, between about 15% w/w and about 50% w/w, or between about 20% w/w and about 40% w/w.

In one embodiment, the total concentration of reactive compounds in the solvent can be about 20% w/w.

In one embodiment, the total concentration of reactive compounds in the solvent can be about 28% w/w.

In one embodiment, the total concentration of reactive compounds in the solvent can be about 37% w/w.

In one embodiment, polymer embolic particles can be prepared from monomers having a single functional group and/or macromers having two or more functional groups suitable for polymerization. Functional groups can include those suitable to free radical polymerization, such as acrylate, acrylamide, methacrylate, vinyl, and methacrylamide. Other polymerization schemes can include, but are not limited to nucleophile/N-hydroxysuccinimide esters, nucleophile/halide, vinyl sulfone/acrylate or maleimide/acrylate. Selection of the monomers is governed by the desired chemical and mechanical properties of the resulting particle.

The prepolymer solution or components in the appropriate solvent can be polymerized by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the monomer solution. In some embodiments, free radical polymerization of the polymerizable components requires an initiator to start the reaction. In one embodiment, the cross-linking method utilizes azobisisobutyronitrile (AIBN) or another water soluble AIBN derivative (2,2'-azobis(2-methylpropionamidine) dihydrochloride). Other cross-linking agents useful according to the present description include N,N,N',N'-tetramethylethylenediamine, ammonium persulfate, benzoyl peroxides, and combinations thereof, including azobisisobutyronitriles. In yet another embodiment the initiator is the combination of N,N,N',N'-tetramethylethylenediamine and ammonium persulfate at a concentration of 5% w/w and 1.8% w/w or 10% w/w and 2.5% w/w, respectively.

In one embodiment, the prepolymer solution can be prepared by dissolving macromer(s), monomer(s), crosslinker(s), and initiator(s) in the solvent. The embolic particles can be prepared by emulsion polymerization in some embodiments. A non-solvent for the prepolymer solution, typically mineral oil when the monomer solvent is water, may be sonicated or sparged with inert gas to remove any entrapped oxygen. The mineral oil and a surfactant can be added to the reaction vessel. An overhead stirrer is placed in the reaction vessel. The reaction vessel is then sealed, degassed under vacuum, and sparged with argon. The initiator component, such as in one non-limiting embodiment N,N,N',N'-tetramethylethylenediamine, is added to the reaction vessel and stirring commenced. Ammonium persulfate can be added to the polymerization solution and both are then added to the reaction vessel, where the stirring suspends droplets of the polymerization solution in the mineral oil.

The rate of stirring can affect the size of the resulting embolic particles. In some embodiments, faster stirring can produce smaller particles and slower stirring can produce larger particles. Stirring rates can be about 100 rpm, about 200 rpm, about 300 rpm, about 400 rpm, about 500 rpm, about 600 rpm, about 700 rpm, about 800 rpm, about 900 rpm, about 1,000 rpm, about 1,100 rpm, about 1,200 rpm, about 1,300 rpm, between about 200 rpm and about 1,200 rpm, between about 400 rpm and about 1,000 rpm, at least about 100 rpm, at least about 200 rpm, at most about 250 rpm, at most about 500 rpm, at most about 1,000 rpm, at most about 1,300 rpm, or at most about 1,200 rpm to produce particles with desired diameters. In one embodiment, stirring rates can range from 200 to 1,200 rpm to produce particles with diameters ranging from 10 to 1,500 microns.

Polymerization can be allowed to proceed as long as necessary to produce particles. Polymerization can be allowed to proceed for about 1 hr, 2 hrs, 2.5 hrs, 3 hrs, 4 hrs, 5 hrs, 6 hrs, 7 hrs, 8 hrs, 9 hrs, 10 hrs, 11 hrs, 12 hrs, 18 hrs, 24 hrs, 48 hrs, 72 hrs, 96 hrs, between about 1 hr and about 12 hrs, between about 1 hr and about 6 hrs, between about 4 hrs and about 12 hrs, between about 6 hrs and about 24 hrs, between about 12 hrs and about 72 hrs, or at least about 6 hours.

Polymerization can be run at a temperature to produce embolic particles with desired diameters. Polymerization can be run at a temperature of about 10° C., about 15° C., about 20° C., about 25° C., about 30° C., about 35° C., about 40° C., about 45° C., about 50° C., about 60° C., about 70° C., about 80° C., about 90° C., about 100° C., between about 10° C. and about 100° C., between about 10° C. and about 30° C., at least about 20° C., at most about 100° C., or at about room temperature. In one embodiment, polymerization occurs at room temperature.

After the polymerization is complete, the polymeric embolic particles can be washed to remove any solute, mineral oil, unreacted monomer(s), unreacted crosslinker(s), unreacted macromer(s), and/or unbound oligomers. Any solvent may be utilized, but care should be taken if aqueous solutions are used to wash particles with linkages susceptible to hydrolysis. Preferred washing solutions include acetone, hexane, alcohols, water+surfactant, water, and saline. In another embodiment, the washing solution is a combination of hexane followed by water. In another embodiment, the washing solution is saline. In further embodiments, the washing solution is water and a surfactant.

Optionally, the washed embolic particles can then be dyed to permit visualization before injection into a microcatheter. A dye bath can be made by dissolving sodium carbonate and the desired dye in water. Embolic particles are added to the dye bath and stirred. After the dying process, any unbound dye is removed through copious washing. After dying and additional washing, the microspheres are packaged into vials or syringes, and sterilized.

Dyes can include any of the dyes from the family of reactive dyes which bond covalently to the embolic particles. Dyes can include reactive blue 21, reactive orange 78, reactive yellow 15, reactive blue No. 19, reactive blue No. 4, C.I. reactive red 11, C.I. reactive yellow 86, C.I. reactive blue 163, C.I. reactive red 180, C.I. reactive black 5, C.I. reactive orange 78, C.I. reactive yellow 15, C.I. reactive blue No. 19, C.I. reactive blue 21, any of the color additives approved for use by the FDA part 73, subpart D, or any dye that can irreversibly bond to the polymer matrix of the embolic particles.

Desired treated polymer particle diameters can be about 10 µm, about 20 µm, about 30 µm, about 40 µm, about 50 µm, about 100 µm, about 200 µm, about 300 µm, about 400 µm, about 500 µm, about 600 µm, about 700 µm, about 800 µm, about 900 µm, about 1,000 µm, about 1,100 µm, about 1,200 µm, about 1,300 µm, about 1,400 µm, about 1,500 µm, about 1,600 µm, about 1,700 µm, about 1,800 µm, about 1,900 µm, about 2,000 µm, between about 50 µm and about 1,500 µm, between about 100 µm and about 1,000 µm, at least about 50 µm, at least about 80 µm, less than about 600 µm, less than about 1,000 µm, less than about 1,200 µm, or less than about 1,500 µm. In one embodiment, the diameter is less than about 1,200 µm.

Desired expanded polymer particle diameters can be about 80 µm, about 100 µm, about 200 µm, about 400 µm, about 500 µm, about 600 µm, about 700 µm, about 800 µm, about 900 µm, about 1,000 µm, about 1,100 µm, about 1,200 µm, about 1,300 µm, about 1,400 µm, about 1,500 µm, about 1,600 µm, about 1,700 µm, about 1,800 µm, about 1,900 µm, about 2,000 µm, about 2,100 µm, about 2,200 µm, about 2,300 µm, about 2,400 µm, about 2,500 µm, about 2,600 µm, about 2,700 µm, about 2,800 µm, about 2,900 µm, about 3,000 µm, about 3,100 µm, about 3,200 µm, about 3,300 µm, about 3,400 µm, about 3,500 µm, about 3,600 µm, about 3,700 µm, about 3,800 µm, about 3,900 µm, about 4,000 µm, between about 80 µm and about 3,600 µm, between about 400 µm and about 4,000 µm, at least about 400 µm, at least about 2,000 µm, less than about 3,000 µm, less than about 3,500 µm, less than about 4,000 µm, or less than about 3,700 µm. In one embodiment, the expanded polymer particle diameter is about 3,600 µm.

In one embodiment, the concentration of macromer(s) in the final embolic particle products can be about 58% w/w.

In one embodiment, poly(ethylene glycol) diacrylamide is present in the final embolic particle products at about 58% w/w.

In one embodiment, the crosslinker can be N,N'-methylenebisacrylamide.

In other embodiments, no crosslinker is included in the desiccated embolic particle products.

In one embodiment, the concentration of one or more monomers in the final embolic particle products can be about 42% w/w.

In one embodiment, the one or more monomers can be sodium acrylate and 2-amino ethyl methacrylate.

In one embodiment, the one or more monomers can be sodium acrylate.

A skilled artisan understands how to calculate final concentrations based on amount in solvent already discussed.

The embolic particles can then be treated to delay the rate at which they expand in a physiological environment. For embolic particles containing acidic moieties, incubation in acidic solution is performed. For embolic particles containing basic moieties, incubation in basic solution is performed. Alternatively, incubation in sodium chloride solutions with higher osmolarity than physiological may decrease the diameter of the embolic particles.

Another method is to formulate the embolic particles with ionic sensitivity. The embolic can be packaged in a concentrated saline solution with a much higher salt concentration than the human body, thus shrinking the embolic. When delivered to the body, the osmotic balance will be restored to the embolic particles as the concentrated saline solution washes away by dilution from the blood. Thus, the embolic particles become exposed to a lower ionic strength environment, causing them to swell to a larger diameter.

A third method is to dehydrate the embolic particles and acid treat them so that they become responsive to physiologic pH. The embolic particles can then be packaged in a low pH, aqueous solution, such as water, or a non-aqueous, biocompatible solution such as mineral oil, alcohol, poly (ethylene glycol) 400, dimethyl sulfoxide, or lipiodol for delivery.

A fourth method is to dehydrate the embolic particles and basic treat them so that they become responsive to physiologic pH. The embolic particles can then be packaged in a high pH, aqueous solution, such as water, or a non-aqueous, biocompatible solution such as mineral oil, alcohol, poly (ethylene glycol) 400, dimethyl sulfoxide, or lipiodol for delivery.

The final polymer embolic particle preparation is delivered to the site to be embolized via a catheter or similar delivery device. In some embodiments, a radiopaque contrast agent is thoroughly mixed with the particle preparation in a syringe and injected through a catheter until blood flow is determined to be occluded from the site by interventional imaging techniques.

The embolic particles described herein can be sterilized without substantially degrading the polymer. After sterilization, at least about 50%, about 60%, about 70%, about 80%, about 90%, about 95% about 99% or about 100% of the polymer can remain intact. In one embodiment, the sterilization method can be autoclaving and can be utilized before administration.

The embolic particles can remain substantially stable once injected. For example, the polymer particles can remain greater than about 60%, about 70% about 80%, about 90%, about 95%, about 99% or about 100% intact after about 5 days, about 2 weeks, about 1 month, about 2 months, about 6 months, about 9 months, about a year, about 2 years, about 5 years, about 10 years, or about 20 years.

The polymer particles described herein can be compressible yet durable enough not to break apart or fragment. Substantially no change in circularity or diameter of particles may occur during delivery through a microcatheter. In other words, after delivery through a microcatheter, the polymer particles described herein remain greater than about 60%, about 70%, about 80%, about 90%, about 95%, about 99% or about 100% intact yet expand to a size larger than when delivered.

The embolic particles can be cohesive enough to stick to tissue and/or remain in place through friction with the tissue. In other embodiments, the particles can act as a plug in a vessel held in place by the flow and pressure of blood.

The embolic particles described herein can have a characteristic expansion time and that characteristic expansion time can be predictable and/or predetermined. This characteristic expansion time can be the amount of time required for the embolic particles to expand from their initial or first diameter to their larger, second expanded diameter. This time can be about 5 min, about 10 min, about 15 min, about 20 min, about 25 min, about 30 min, between about 5 min and about 20 min, between about 10 min and about 25 min, between about 5 min and about 30 min, at least about 5 min, or at least about 10 min.

Also, this characteristic expansion time can provide a user, for example a physician, sufficient time to deliver the particles to the desired in situ location without the particles expanding and clogging a microcatether or other deliver device.

In one embodiment, a desiccated polymeric embolic particle can include a reaction product of a polyether and sodium acrylate. In another embodiment, a polymeric embolic particle can include a polyether at about 58% w/w and sodium acrylate at about 42% w/w.

In another embodiment, a desiccated polymeric embolic particle can include a reaction product of a polyether, aminopropyl methacrylamide, and sulfopropyl acrylate. In another embodiment, a polymeric embolic particle can include a polyether at about 40% w/w, aminopropyl methacrylamide at about 1% w/w, and sulfopropyl acrylate at about 59% w/w.

The following represent non-limiting embodiments.

Embodiment 1: An embolic composition comprising: embolic particles including acidic groups that are treated with a low pH solution to form treated embolic particles, wherein the treated embolic particles have a first diameter and a second diameter, and wherein the second diameter is larger than the first diameter when the treated polymer particle is subjected to a physiological condition.

Embodiment 2: The embolic composition of Embodiment 1, wherein the first diameter is between about 40 µm and about 1,200 µm.

Embodiment 3: The embolic composition of Embodiment 1 or 2, wherein the first diameter is smaller than the diameter of a microcatheter.

Embodiment 4: The embolic composition of Embodiment 1, 2, or 3, wherein the second diameter is between about 80 µm and about 3,600 µm.

Embodiment 5: The embolic composition of Embodiment 1, 2, 3, or 4, wherein the second diameter is larger than the diameter of the microcatheter.

Embodiment 6: The embolic composition of Embodiment 1, 2, 3, 4, or 5, wherein the embolic particles include a reaction product of a prepolymer solution including at least one macromer and at least one monomer including ionic groups.

Embodiment 7: The embolic composition of Embodiment 1, 2, 3, 4, 5, or 6, wherein the monomer containing ionic groups is sodium acrylate.

Embodiment 8: The embolic composition of Embodiment 1, 2, 3, 4, 5, 6, or 7, wherein the at least one macromer is poly(ethylene glycol) diacrylamide, poly(ethylene glycol) diacrylate, poly(ethylene glycol) dimethacrylate, poly(ethylene glycol) dimethacrylamide, or a combination thereof.

Embodiment 9: The embolic composition of Embodiment 1, 2, 3, 4, 5, 6, 7, or 8, wherein the prepolymer solution further includes a biodegradable crosslinker.

Embodiment 10: The embolic composition of Embodiment 9, wherein the biodegradable crosslinker has a structure:

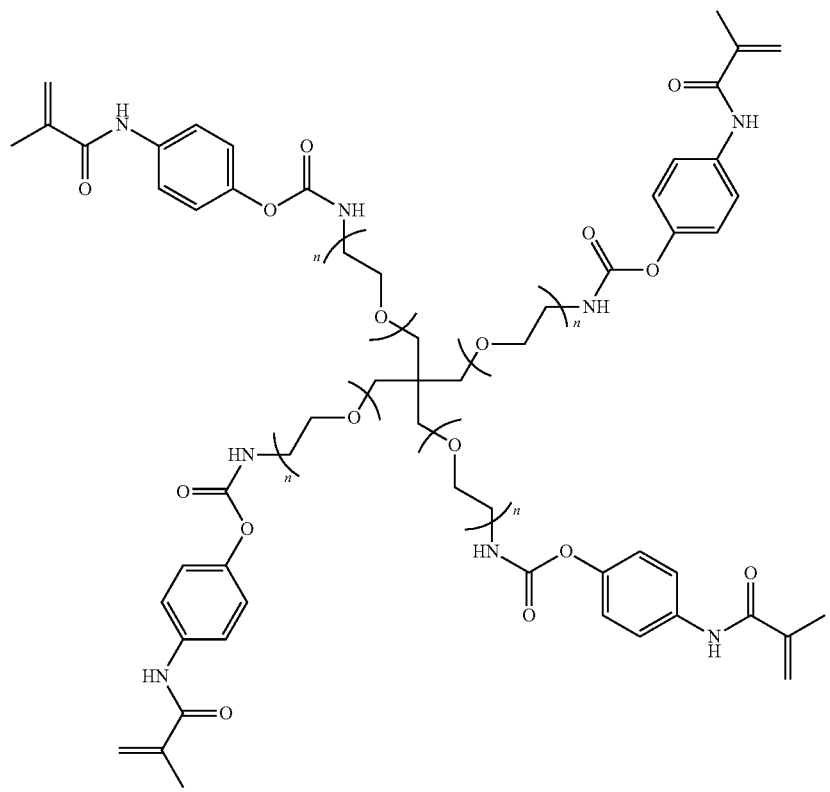
wherein each n is independently 1-20;
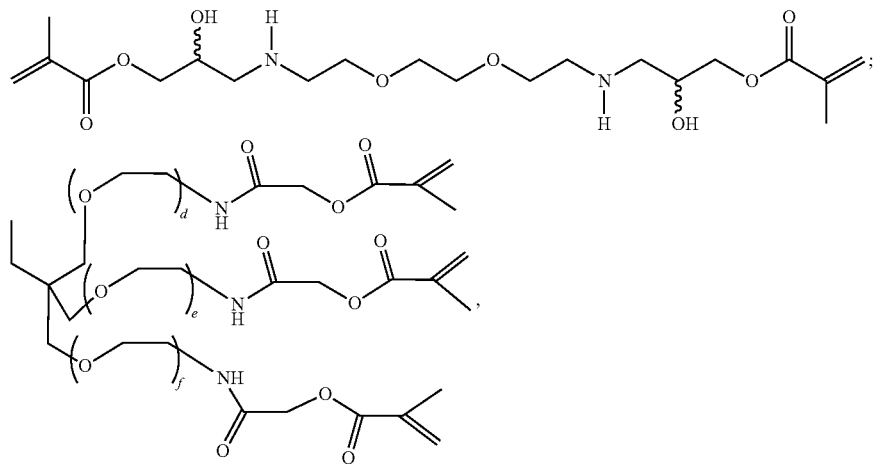
wherein d, e, f, and g are each independently 1-20; or
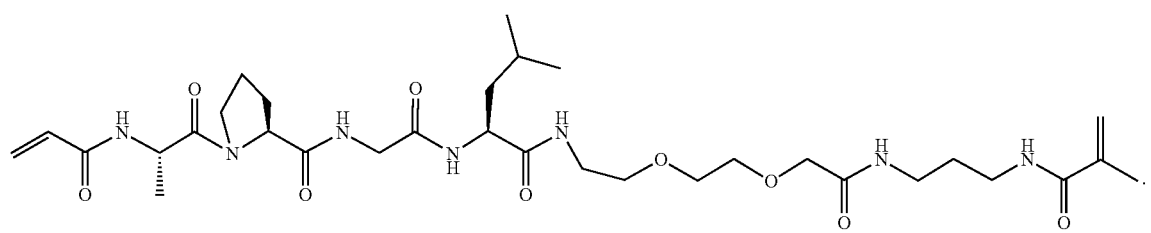 [SMILES: C=CC(=O)N[C@@H](C)C(=O)N1CCC[C@H]1C(=O)NCC(=O)N[C@@H](CC(C)C)C(=O)NCCOCCOCC(=O)NCCCNC(=O)C(=C)C]

Embodiment 11: The embolic composition of Embodiment 1, 2, 3, 4, 5, 6, 7, 8, or 9, wherein the embolic particles further include a visualization agent.

Embodiment 12: The embolic composition of Embodiment 11, wherein the visulaization agent is an monomer including a visualization agent and has a structure

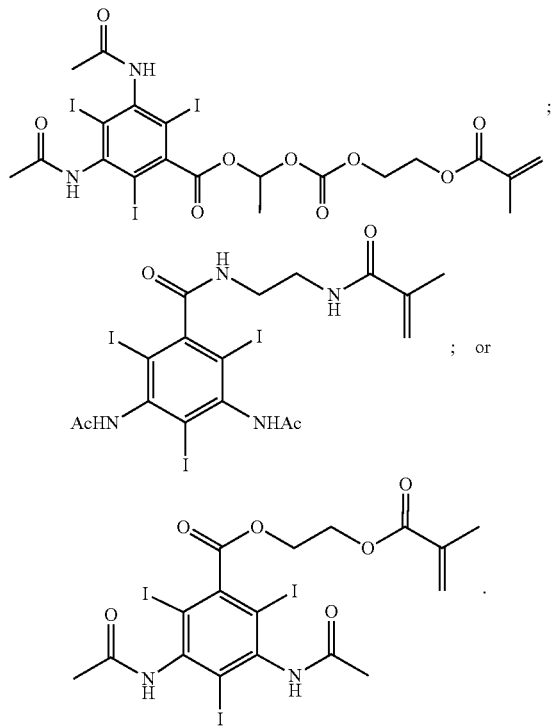

Embodiment 13: The embolic composition of Embodiment 1, 2, 3, 4, 5, 6, 7, 8, 9, 10, 11, or 12, wherein the physiological condition is physiological pH.

Embodiment 14: A method of making polymer particles comprising: treating polymer particles formed by reacting a prepolymer solution including at least one macromer, an acrylic monomer, and an initiator in non-solvent to form treated polymer particles; wherein the treated polymer particle has a first diameter and a second diameter, wherein the second diameter is larger than the first diameter when the treated polymer particle is subjected to a physiological condition.

Embodiment 15: The method of Embodiment 14, wherein the non-solvent is a mineral oil, hexane, or water.

Embodiment 16: The method of Embodiment 14 or 15, wherein the initiator is ammonium persulfate, tetramethylethylene diamine, or a combination thereof.

Embodiment 17: The method of Embodiment 14, 15, or 16, wherein the first diameter is between about 40 μm and about 1,200 μm.

Embodiment 18: The method of Embodiment 14, 15, 16, or 17, wherein the first diameter is smaller than the diameter of a microcatheter.

Embodiment 19: The method of Embodiment 14, 15, 16, 17, or 18, wherein the second diameter is between about 80 μm and about 3,600 μm.

Embodiment 20: The method of Embodiment 14, 15, 16, 17, 18, or 19, wherein the second diameter is larger than the diameter of the microcatheter.

Embodiment 21: The method of Embodiment 14, 15, 16, 17, 18, 19, or 20, wherein the at least one macromer is poly(ethylene glycol) diacrylamide, poly(ethylene glycol) diacrylate, poly(ethylene glycol) dimethacrylate, poly(ethylene glycol) dimethacrylamide, or a combination thereof.

Embodiment 22: The method of Embodiment 14, 15, 16, 17, 18, 19, 20, or 21, wherein the treating is acid treating and the monomer containing ionic groups is sodium acrylate.

Embodiment 23: The method of Embodiment 14, wherein the treating is base treating and the monomer containing ionic groups includes amino groups.

Example 1

Biostable Embolic Particle Preparation

A prepolymer solution was prepared by dissolving 9.2 g poly(ethylene glycol) 10,000 diacrylamide and 6.6 g sodium acrylate in 39.8 g of distilled water. This solution was filtered and flushed with argon. Then, 500 mL of mineral oil was sparged with argon for 6 hr in a sealed reaction vessel equipped with an overhead stirring element. N,N,N',N'-tetramethylethylenediamine (3 mL) was added to the reaction vessel and overhead stirring started at 230 RPM. An initiator solution was made by dissolving 1.0 g ammonium persulfate in 2.0 g distilled water. The solution was filtered and 1 mL added to the prepolymer solution. After mixing, the solution was added to the reaction vessel. After 5 to 10 min, 0.1 mL of SPAN®80 was added and the resulting suspension was allowed to polymerize over 4 hrs.

Example 2

Purification of the Embolic Particle Preparation

After the polymerization was complete, the mineral oil was decanted from the reaction vessel and the polymer embolic particles were washed four times with fresh portions of hexane to remove the mineral oil. The particles were then transferred to a separatory funnel with phosphate buffered saline (PBS) and separated from residual mineral oil and hexane. The resulting mixture was washed twice with PBS.

To dye the embolic particles, 50 g of sodium carbonate and 0.1 g reactive black 5 dye (Sigma-Aldrich Co. LLC, St. Louis, MO) were dissolved in 1,000 mL of de-ionized water. Then, drained embolic particles were added and allowed to stir for 1 hr. The dyed particle preparation was washed with de-ionized water until all residual dye was removed.

The dyed embolic particles were separated in sizes using sieving. Sieves were stacked from the largest size (on top) to the smallest size (on bottom). A sieve shaker was utilized to aid the sieving process. The embolic particles were placed on the top sieve along with PBS. Once all the embolic particles had been sorted, they were collected and placed in bottles according to their size.

Dyed particles were incubated in 0.1 N HCl for 30 minutes to protonate available carboxylic acid groups. Significant decrease in the diameter was observed. The acid was removed and replaced with distilled water for storage.

Example 3

Preparation of a Biodegradable Crosslinker

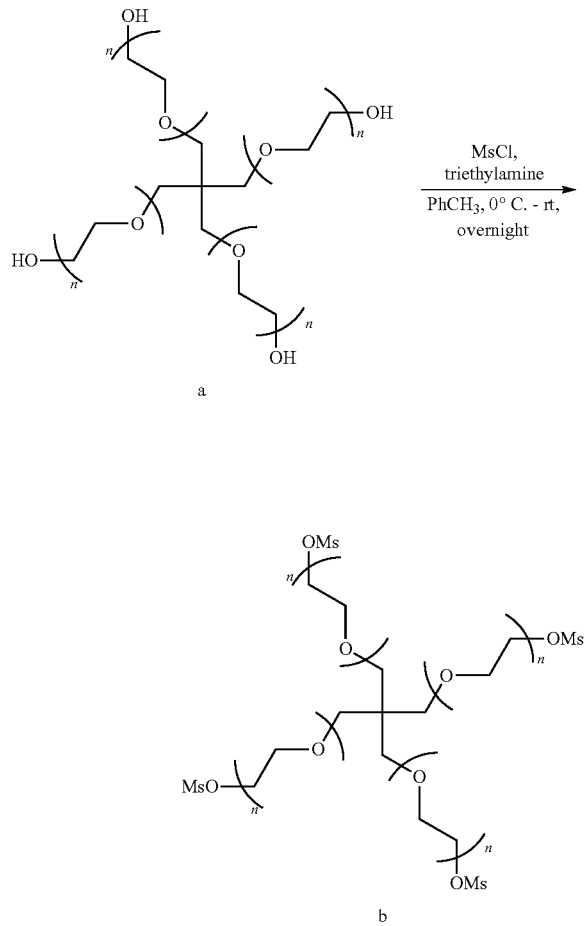

a b

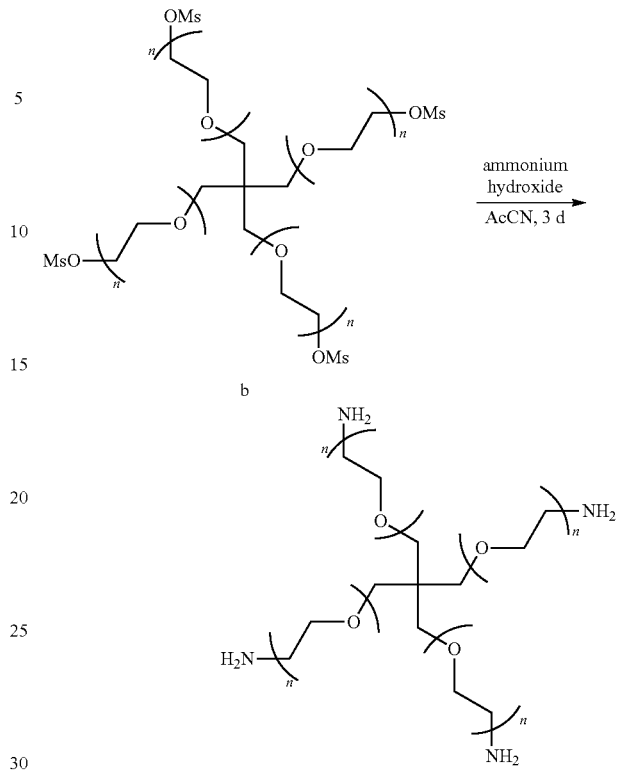

b c

Preparation of tetraamino pentaerythritol (c): To a solution of ammonium hydroxide (30%, 1250 mL, 22.02 mol) was added dropwise tetramesyl pentaerythriol (b, 86.37 g, 77.8 mmol) in anhydrous acetonitrile (500 mL). The reaction was stirred under room temperature for three days. Upon completion, it was degassed for 2 days using an air pump. Then the pH of the residue was adjusted to 14 using 0.1 M NaOH aqueous solution. The aqueous phase was extracted with dichloromethane (500 mL×1, and 1 L×1). The organic phase was then dried over sodium sulfate and concentrated using a rotary evaporator to afford the product as a pale yellow oil (56.31 g).

Preparation of tetramesyl pentaerythritol (b): To a 3 L three-neck round bottom flask fitted with a Dean-Stark trap was added pentaerythritol (a, MW~797 g/mol, 99.9 g, 125 mmol) and toluene (1.5 L) sequentially. The solution was subjected to an azeotrope distillation and water was removed from the Dean-Stark trap. The flask was cooled to room temperature before triethylamine (94.6 mL, 530 mmol) was added. Then the flask was placed in a 0° C. ice bath. A 250 mL addition funnel was attached to the flask. To the addition funnel was added anhydrous toluene (80 mL) and mesyl chloride (40 mL, 530 mmol) sequentially. The mesyl chloride solution was added dropwise to the cooled solution. The reaction was left to stir at room temperature overnight, resulting in the formation of a white precipitate. At the end of the reaction, the solution was filtered over a fritted glass funnel to remove the precipitate. The filtrate was concentrated using a rotary evaporator to afford the crude material as a pale yellow oil (86.37 g).

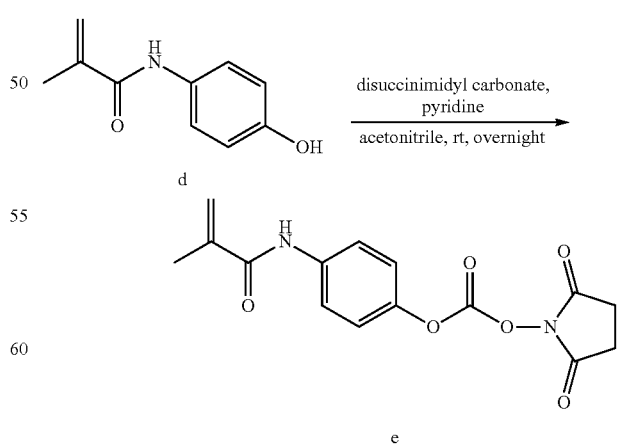

d e

Preparation of NHS-activated (4-hydroxyphenylmethacrylamide) (e): To a solution of (4-hydroxyphenylmethacrylamide) (d, 10 g, 56.4 mmol) in anhydrous acetonitrile (39.5 mL) was added anhydrous pyridine (9.9 mL, 113 mmol) and disuccinimidyl carbonate (36.1 g, 141 mmol) sequentially. The solution was stirred for 18 hours at room temperature. Upon completion, the reaction was poured over dichloromethane (40 mL) and filtered over a Buchner funnel. The filtrate was collected and the solvent was removed on a rotary evaporator. The residue was suspended in 30 mL ethyl acetate. The ethyl acetate fraction was washed with 5% citric acid solution (30 mL×2) and saturated NaCl solution (30 mL×1) before being dried over $Na_2SO_4$. The solvent was removed on a rotary evaporator to afford the product as a pinkish solid (12.96 g, 72.2% yield).

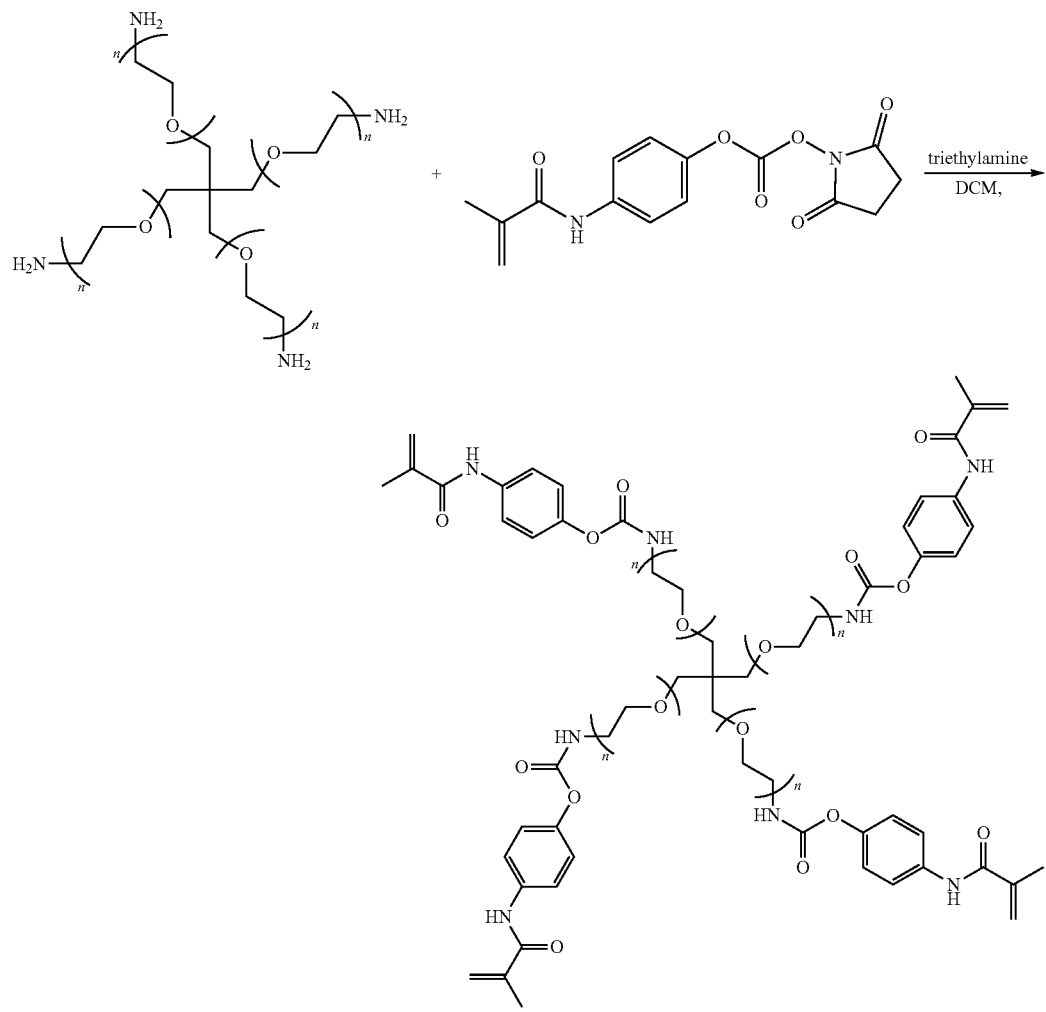

Preparation of a biodegradable crosslinker (f): To a solution of tetraamino pentaerythritol (c, 10.0 g, 12.6 mmol) and trimethylamine (7.0 mL, 50.4 mmol) in dichloromethane (67 mL) was added NHS-activated (4-hydroxyphenylmethacrylamide) (e, 16.0 g, 50.4 mmol) under argon. The solution was stirred for 3 hours 15 minutes. Upon completion, it was passed through a silica gel plug. The elution was using a rotary evaporator, and the residue was separated using flash chromatography to afford the product.

Example 4

Preparation of a Biodegradable Crosslinker

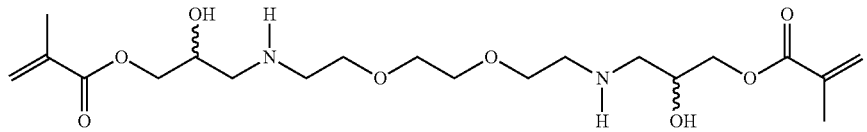 [SMILES: C=C(C)C(=O)OCC(O)CNCCOCCOCCNCC(O)COC(=O)C(=C)C]

To 10 g (67.6 1 mnol) of 2,2'-ethylenedioxy-bis-ethylamine was added 10 g (70.4 mmol) of glycidyl methacrylate and 3.0 g of silica gel (Aldrich 645524, 60 Angstrom 200-425 mesh), with good stirring. After stirring for 1 hr, another 9 g (63.4 mmol) of glycidyl methacrylate was added and the suspension was stirred for an additional 1.5 hr. The reaction mixture was diluted with 200 mL of reagent grade chloroform and filtered through a 600 mL fritted glass Buchner funnel of medium porosity, to remove silica gel. LC-MS analysis of the resultant chloroform solution showed almost no mono-glycidyl amino alcohol and mostly bis-glycidyl amino alcohol at (M+H)+ 433.2 and was concentrated to about 50 g in vacuo. The resultant heavy syrup was diluted to 100 mL with acetonitrile and stored at −80° C.

Example 5

Preparation of a Biodegradable Crosslinker

TMP-Chloroacetamide (E): To 13.2 g of TMP amine in 250 mL of dry THF was added 6.32 g (80 mmols) of pyridine and this solution was added to 6.44 g of chloroacetyl chloride in 250 mL of THF with good stirring, at 4-1° C. under Ar. After stirring for 15 min, the reaction mixture was warmed to room temperature and the THF and other volatile materials were removed in vacuo. The resulting solids were dissolved into 200 mL of chloroform, washed with 100 mL of saturated aqueous sodium bicarbonate, dried over magnesium sulfate, and the solvent was removed in vacuo.

TMP-NH-Gly-Methacrylate (F): Approximately 15 grams of (E) was dissolved into 75 mL of anhydrous DMF and added 18 g of cesium methacrylate was added. The resulting suspension heated at 40-50° C. for 2 hr.

After precipitation with 500 mL of chloroform, the inorganic salts were collected by filtration and the filtrate was concentrated to an oil in vacuo to give 18 g of a reddish brown oil. This oil was polymerized with AIBN at 80° C., in isopropyl alcohol to a nice hard pellet. Chromatography on 6 g of this through a plug of the above silica with 1,200 mL of 2-20% methanol in chloroform, gave 6 g of light red colored material. This material can be used to prepare polymer filaments.

The material can have a structure

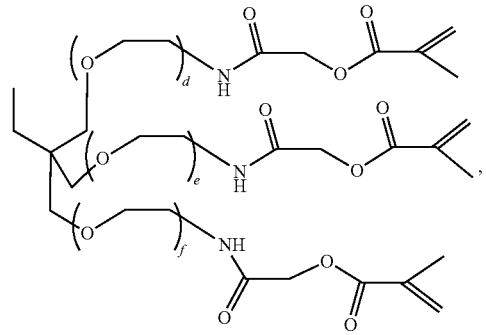

wherein d, e, f, and g are each independently 1-20.

Example 6

Preparation of a Biodegradable Crosslinker

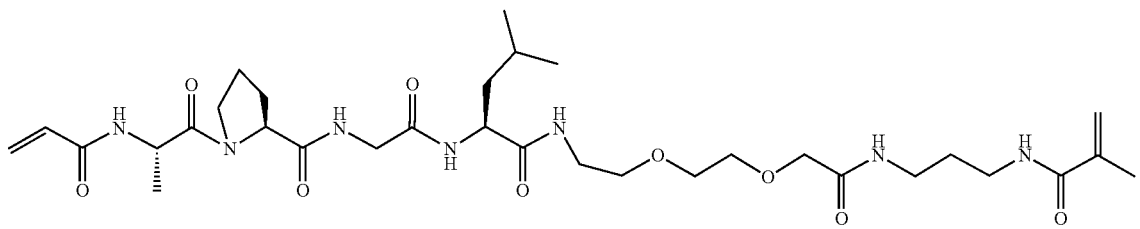 [SMILES: C=CC(=O)N[C@@H](C)C(=O)N1CCC[C@H]1C(=O)NCC(=O)N[C@@H](CC(C)C)C(=O)NCCOCCOCC(=O)NCCCNC(=O)C(=C)C]

To 653 mg (1 mmol) of tetrapeptide Alanine-Proline-Glycine-Leucine (APGL) in 5 mL dry DMF was added 190 mg (1.1 mmol) of APMA-HCl, followed by 174 µL (1 mmol) of DIPEA, at room temperature with good stirring, under Ar. After 2 hr, the reaction mixture was treated with 20 mg of BHT and briefly exposed to air. LC-MS analysis showed (M+H)+ at 680 and (M+Na)+ at 702. Then, 5 mL of the reaction mixture was added dropwise to 200 mL of ether with good stirring and the solids which formed were collected by centrifugation. The resulting pellet was dissolved into 20 mL of (CHCl$_3$/MeOH/MeOH+5% aqueous ammonia) 90/5/5, and applied to 50 g of silica gel in a 5×20 cm column (Aldrich 645524, 60 Angstrom 200-425 mesh). The silica gel column was developed with 500 mL of (CHCl$_3$/MeOH/MeOH with 5% aqueous ammonia), 90/5/5. The peptide containing eluent (TLC, same solvent) was concentrated in vacuo to yield 110 mg of pale yellow oil, LCMS, as above. The pale yellow oil was dissolved in 10 mL of methanol and stored at –80° C.

Example 7

Preparation of a Degradable Radiopaque Monomer

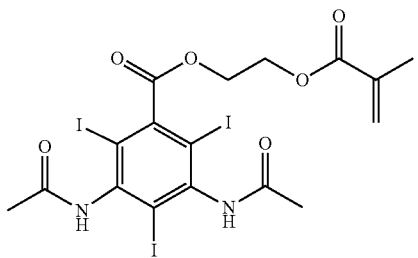 [SMILES: C=C(C)C(=O)OCCOC(=O)c1c(I)c(NC(C)=O)c(I)c(NC(C)=O)c1I]

Tetrabutylammonium diatrizoate: To a stirring suspension of diatrizoic acid (50 g, 81.4 mmol) in methanol (552 mL) was slowly added tetrabutylammonium hydroxide (40% aqueous solution, 52.8 mL). The turbid suspension turned clear after the addition of tetrabutylammonium hydroxide was finished. The solvent was removed using a rotary evaporator to obtain a cream-colored viscous residue. To this residue was added an appropriate amount of toluene, which was then removed using a rotary evaporator. Toluene was added to the residue once more and removed again. The solid obtained was dried in a vacuum oven overnight at 40° C. to afford a white solid (64.1 g, 92% yield). (WO 95/19186)

Diatrizoyl HEMA: To a stirring solution of KI (796.8 mg, 4.38 mmol) and 2-chloro ethylmethacrylate (4.32 mL, 32.1 mmol) in anhydrous DMF (122.6 mL) was added tetrabutylammonium diatrizoate (25 g, 29.2 mmol) under argon. The flask was then placed in a 60° C. oil bath. Additional KI (199 mg) and 2-chloro ethylmethacrylate (1 mL) was added to the reaction at 13 hours, 38 hours and 41 hours reaction times. The reaction was pulled out of the oil bath at 44 hours and cooled under room temperature. The reaction was poured over saturated NaHCO$_3$ aqueous solution (120 mL) and a white precipitate formed. The aqueous phase was extracted once with a mixture of ethyl acetate (280 mL) and methanol (50 mL). The organic phase was washed with saturated sodium chloride aqueous solution (300 mL×1). The organic phase was subjected to rotary evaporation to obtain a cream-colored wet solid. The solid was suspended in a mixture of methyl tert-butyl ether and chloroform (7:3, v/v), and the resulting suspension was filtered to obtain a white solid. The solid dried under reduced pressure to obtain the first crop of product as a white solid (11.898 g). The previous NaHCO$_3$ phase was filtered and a white solid was collected. The solid was washed with a mixture of methyl tert-butyl ether and chloroform (7:3, v/v) and dried under reduced pressure to afford the second crop (3.071 g). The first and second crops were combined to afford the final product as a white solid (14.969 g, 70.6% yield).

Example 8

Preparation of a Degradable Radiopaque Monomer

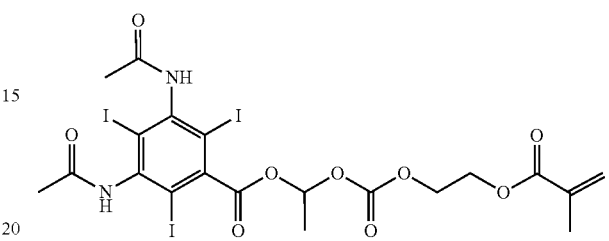

To 400 mL of methanol was added 104 g (170 mmol) of diatrizoic acid followed by 28 g of cesium carbonate (65 mmol). After stirring for 45 min the methanol was removed in vacuo and the solids suspended in 500 mL of diethyl ether. The solids were then collected and dried on a Buchner funnel and further dried in vacuo, to yield 120 g, (95%) (Cesium Diatriozate, 1).

To 24 mL of HEMA (200 mmol) in 1,000 mL of dry ether was added 16.8 mL (213 mmol) of pyridine at 4-10° C., under Ar. To this solution was added 21.3 mL (200 mmol) of 1-chloroethyl chlorocarbonate, drop wise with stirring over 0.5 hr. After stirring 0.5 hr at 4-10° C., the heavy precipitate was removed by filtration and the filtrate was concentrated to oil in vacuo, yielding 44 g (100%) (HEMA-1-Chloroethyl carbonate, 2).

To 44 g (200 mmol) of (2) in 400 mL of anhydrous DMF was added 30 g (40 mmol) of (1) at 100° C. under Ar, with good stirring. After 15 min another 40 g (54 mmol) of (1) was added at 100° C., under Ar, with good stirring followed by a final 30 g (40 mmol), under the same conditions, for a total of 110 g (1) (134 mmol). The reddish brown reaction mixture was heated at 100° C. for an additional hour and the solvent was removed in vacuo. The reddish brown solid residue was suspended in 1,000 mL of dry ether and the solids collected on a Buchner funnel. After the solids were dried in vacuo, they were suspended in 500 mL distilled water at 2,000 rpm and the mixture pH was adjusted to 8-9 with cesium carbonate. After stirring for 10 min, the suspension was filtered and the solids washed 3 times with 100 mL of distilled water, dried overnight in vacuo and crushed to a fine powder. Solid residue was again suspended in 1,000 mL of dry ether and the solids were collected on a Buchner funnel. After the solids were dried in vacuo again and crushed to a fine powder again, they were purified by silica gel chromatograph using a 1.5 Kg column and a 0-10% gradient of methanol in dichloromethane, over 1 hr. This yielded 26 grams (18%), very pale yellow crystalline solid (1-((2-(methacryloyloxy)ethoxy)carbonyloxy)ethyl-3,5-diacetamido-2,4,6-triiodobenzoate, 3).

Example 9

Preparation of a Non-Degradable Radiopaque Monomer

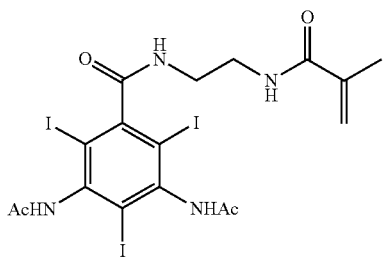 [SMILES: C=C(C)C(=O)NCCNC(=O)c1c(I)c(NC(C)=O)c(I)c(NC(C)=O)c1I]

Diatriazoyl Acetate (A): To 30.8 g of diatrizoic acid suspended in 100 mL of acetic anhydride was added 2 g of concentrated sulfuric acid and the resulting suspension stirred at 90 degrees centigrade for one hour before the reaction mixture was cooled to room temperature and then poured onto 500 g of ice. After agitating the ice for 15 min, the oily mass was treated with 100 mL of half saturated sodium bicarbonate whilst agitating. The solids which had formed were collected on a Buchner funnel and dried overnight in vacuo to give 9 g of light brown diatriazoyl acetate solids.

Diatriazoyl Chloride (B): Nine grams of ditriazoyl acetate was suspended in 100 mL of thionyl chloride using overhead stirring. The reaction mixture was brought to reflux in an oil bath and refluxed for one hour. The thionyl chloride was mostly removed in vacuo at 40° C. at which point solids were re-suspended in 100 mL of ethyl acetate which was removed in vacuo. This process was repeated twice more at which point the solids were placed under vacuum overnight.

Ethylenediamine mono-diatriazoyl amide (C): 6.3 g of the acid chloride (10 mmol) in 300 mL of methylene chloride was added to 6.7 grams of ethylene diamine (100 mmol) over one hour with stirring at 4-10° C. under Ar. The formed solids were collected on a Buchner funnel and washed with 100 mL of methylene chloride and dried overnight in vacuo. The dried solids now largely free of ethylenediamine were taken up in 600 mL of water filtered through a fritted disk funnel and the water removed in vacuo. The residue was triturated with acetonitrile which was then evaporated in vacuo to remove traces of water. LC-MS showed 640 which is $(M+Na)^+$ and 656.9, $(M+K)^+$.

Ethylene diamine-1-diatriazoylamide-2-methacrylamide (D): To 650 mg of (C) (1 mmol) suspended in 100 mL of THF/CHCl$_3$/ethanol, 1/3/1 was added 0.18 mL (1.04 mmol) of diisopropylethylamine followed by 0.12 mL (1.26 mmol) of methacryoyl chloride with stirring under Ar. The reaction mixture was stirred for 1 hr at which point reaction mixture was filtered with a fritted Buchner funnel.

TLC with 10% methanol in methylene chloride showed potential product in solids and filtrate. LC-MS of combined filtrate and solids after solvent removal in vacuo showed $(M+H)^+$ at 725.0, $(M+Na)^+$ at 747.0 as well as $(M-H)^-$ at 723.0 and $(M+Na-2H)^-$ at 744.9 all on an HPLC peak at 8.9 min in a 15 min run.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An embolic composition including:
   particles including a reaction product of a prepolymer solution including:
   a polyether macromer; and
   a monomer including a single ethylenic unsaturation,
   wherein the embolic; composition is configured to fit through an inner diameter of a microcatheter.

2. The embolic composition of claim 1, wherein the inner diameter is at most about 0.0155 inch.

3. The embolic composition of claim 1, wherein the inner diameter is at most about 0.0160 inch.

4. The embolic composition of claim 1, wherein the inner diameter is at most about 0.0165 inch.

5. The embolic composition of claim 1, wherein the inner diameter is at most about 0.0170 inch.

6. The embolic composition of claim 1, wherein the inner diameter is at most about 0.0175 inch.

7. The embolic composition of claim 1, wherein the inner diameter is at most about 0.018 inch.

8. The embolic composition of claim 1, wherein the inner diameter is at most about 0.019 inch.

9. The embolic composition of claim 1, wherein the inner diameter is at most about 0.02 inch.

10. The embolic composition of claim 1, wherein the polyether macromer is a poly(ethylene glycol) diacrylamide macromer, a poly(ethylene glycol) diacrylate macromer, a poly(ethylene glycol) dimethacrylate macromer, a poly(ethylene glycol) dimethacrylamide macromer, or a combination thereof.

11. The embolic composition of claim 1, further comprising a visualization agent.

12. The embolic composition of claim 11, wherein the visualization agent is particles of radiopaque materials or halogen containing monomers.

13. The embolic composition of claim 12, wherein the halogen containing monomer is an iodine containing monomer.

14. The embolic composition of claim 13, wherein the iodine containing monomer has a structure:

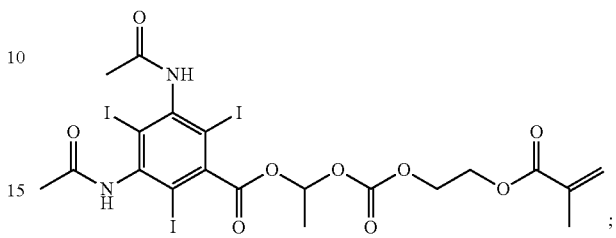

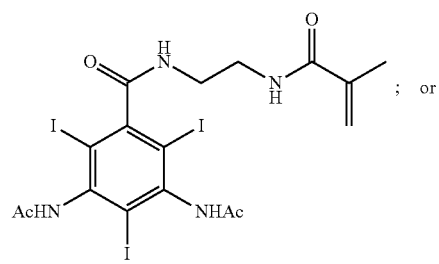

; or

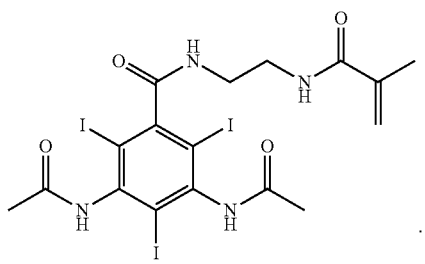

.

15. The embolic composition of claim 12, wherein the particles of radiopaque materials include barium, bismuth, tantalum, platinum, and gold.

16. The embolic composition of claim 12, wherein the particles of radiopaque materials include barium sulfate.

17. The embolic composition of claim 1, wherein the prepolymer solution further includes a crosslinker having a structure

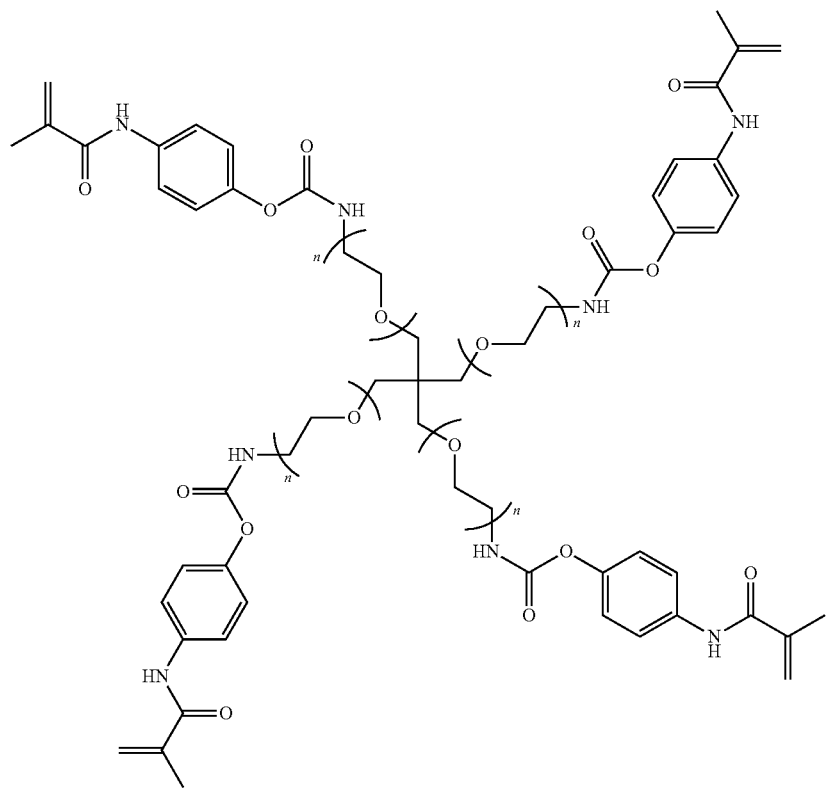
wherein each n is independently 1-20;
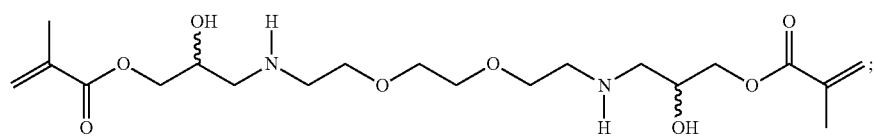
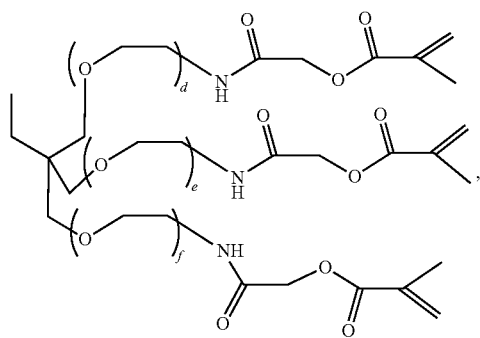
wherein d, e, and f are each independently 1-20;

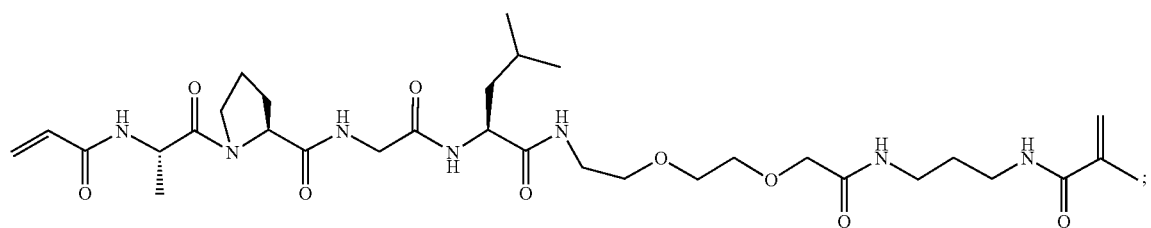 [SMILES: C=CC(=O)N[C@@H](C)C(=O)N1CCC[C@H]1C(=O)NCC(=O)N[C@@H](CC(C)C)C(=O)NCCOCCOCC(=O)NCCCNC(=O)C(=C)C]
or a combination thereof.
18. The embolic composition of claim 1, wherein the embolic particles are substantially spherical.
19. The embolic composition of claim 1, wherein the embolic particles are substantially stable.
20. The embolic composition of claim 1, wherein the embolic particles are substantially biodegradable.
* * * * *